US 8,502,684 B2

(12) United States Patent
Bunza et al.

(10) Patent No.: US 8,502,684 B2
(45) Date of Patent: Aug. 6, 2013

(54) SENSORS AND SYSTEMS FOR DETECTING ENVIRONMENTAL CONDITIONS OR CHANGES

(76) Inventors: Geoffrey J. Bunza, Beaverton, OR (US); Steven W. Hudnut, Beaverton, OR (US)

( * ) Notice: Subject to any disclaimer, the term of this patent is extended or adjusted under 35 U.S.C. 154(b) by 0 days.

(21) Appl. No.: 13/011,781

(22) Filed: Jan. 21, 2011

(65) Prior Publication Data
US 2011/0309937 A1 Dec. 22, 2011

Related U.S. Application Data

(63) Continuation-in-part of application No. 12/902,115, filed on Oct. 11, 2010, now abandoned, which is a continuation of application No. 11/615,313, filed on Dec. 22, 2006, now Pat. No. 7,812,731.

(51) Int. Cl.
*G08B 23/00* (2006.01)
(52) U.S. Cl.
USPC ............... 340/573.5; 340/573.1; 340/572.1
(58) Field of Classification Search
USPC ....................................................... 340/573.5
See application file for complete search history.

(56) References Cited

U.S. PATENT DOCUMENTS

| 4,137,361 | A | 1/1979 | Deffeyes et al. |
| 4,161,564 | A | 7/1979 | Legbandt |
| 4,218,507 | A | 8/1980 | Deffeyes et al. |
| 4,448,637 | A | 5/1984 | Hiraishi et al. |
| 4,545,914 | A | 10/1985 | Graiver et al. |
| 4,547,312 | A | 10/1985 | Graiver et al. |
| 5,018,180 | A | 5/1991 | Shoulders |
| 5,054,047 | A | 10/1991 | Shoulders |
| 5,123,039 | A | 6/1992 | Shoulders |
| 5,148,461 | A | 9/1992 | Shoulders |
| 5,188,890 | A | 2/1993 | Ohashi et al. |
| 5,190,813 | A | 3/1993 | Ohashi et al. |
| 5,236,512 | A | 8/1993 | Rogers et al. |

(Continued)

FOREIGN PATENT DOCUMENTS

| DE | 4444264 C1 | 4/1996 |
| DE | 19525326 C1 | 10/1996 |

(Continued)

OTHER PUBLICATIONS

Finkenzeller, Klaus, "RFID Handbook: Fundamentals and Applications in Contactless Smart Cards and Identification," John Wiley & Sons Ltd., England. (2003) pp. 1-9, 22-23, 26-27, 29-59, 106-112, and 117-119.

(Continued)

*Primary Examiner* — Kerri McNally
(74) *Attorney, Agent, or Firm* — Schwabe, Williamson & Wyatt

(57) ABSTRACT

Sensors and systems for detecting predetermined environmental conditions or changes may include a device capable of providing information. The device may include either a shield or reconfigurable antenna. For example, in a first condition, a shield is configured to prevent communications with the device and, in a second condition, the shield is configured to enable communications with the device. Alternately, in a first condition, a reconfigurable antenna is configured to enable communications with the device and in a second condition the reconfigurable antenna is configured to prevent communications with the device. The shield or reconfigurable antenna may be configured to transition from first conditions to second conditions upon exposure to a predetermined environmental condition or change.

28 Claims, 8 Drawing Sheets

U.S. PATENT DOCUMENTS

| | | |
|---|---|---|
| 5,298,058 A | 3/1994 | Matsui et al. |
| 5,336,869 A | 8/1994 | Kumar |
| 5,356,579 A | 10/1994 | Jennings et al. |
| 5,358,676 A | 10/1994 | Jennings et al. |
| 5,399,413 A | 3/1995 | Katsen et al. |
| 5,462,771 A | 10/1995 | Motoki et al. |
| 5,525,423 A | 6/1996 | Liberman et al. |
| 5,527,850 A | 6/1996 | Katayama et al. |
| 5,549,851 A | 8/1996 | Fukushima et al. |
| 5,557,263 A | 9/1996 | Fisher et al. |
| 5,557,279 A | 9/1996 | D'hont |
| 5,570,082 A | 10/1996 | Mahgerefteh et al. |
| 5,573,610 A | 11/1996 | Koch et al. |
| 5,573,611 A | 11/1996 | Koch et al. |
| 5,635,292 A | 6/1997 | Jennings et al. |
| 5,637,412 A | 6/1997 | Jennings et al. |
| 5,781,110 A | 7/1998 | Habeger, Jr. et al. |
| 5,858,600 A | 1/1999 | Itakura et al. |
| 5,876,586 A | 3/1999 | Fukushima et al. |
| 5,904,671 A | 5/1999 | Navot et al. |
| 5,909,171 A | 6/1999 | Kyrtsos |
| 5,910,766 A | 6/1999 | Evans |
| 5,955,192 A | 9/1999 | Fukushima et al. |
| 5,992,739 A | 11/1999 | Maeder |
| 6,091,607 A | 7/2000 | McKeown et al. |
| 6,097,297 A * | 8/2000 | Fard ............... 340/604 |
| 6,110,651 A | 8/2000 | Fukushima et al. |
| 6,147,662 A | 11/2000 | Grabau et al. |
| 6,154,137 A | 11/2000 | Goff et al. |
| 6,294,997 B1 | 9/2001 | Paratore et al. |
| 6,344,155 B1 | 2/2002 | Kitahara et al. |
| 6,344,309 B2 | 2/2002 | Fukushima et al. |
| 6,346,886 B1 | 2/2002 | De La Huerga |
| 6,356,201 B1 | 3/2002 | Alles |
| 6,373,395 B1 | 4/2002 | Kimsey |
| 6,455,770 B2 | 9/2002 | Pulver |
| 6,463,798 B2 | 10/2002 | Niekerk et al. |
| 6,501,375 B1 | 12/2002 | Weant et al. |
| 6,506,872 B2 | 1/2003 | Kimura et al. |
| 6,541,346 B2 | 4/2003 | Malik |
| 6,582,767 B1 | 6/2003 | Fukushima et al. |
| 6,583,722 B2 | 6/2003 | Jeutter et al. |
| 6,586,931 B2 | 7/2003 | Taicher |
| 6,603,403 B2 | 8/2003 | Jeutter et al. |
| 6,606,247 B2 | 8/2003 | Credelle et al. |
| 6,607,825 B1 | 8/2003 | Wang et al. |
| 6,639,304 B1 | 10/2003 | Oggioni et al. |
| 6,673,999 B1 | 1/2004 | Wang et al. |
| 6,696,937 B1 | 2/2004 | Keifer |
| 6,713,327 B2 | 3/2004 | Leedy |
| 6,713,671 B1 | 3/2004 | Wang et al. |
| 6,753,771 B2 | 6/2004 | Lesesky |
| 6,765,144 B1 | 7/2004 | Wang et al. |
| 6,774,800 B2 | 8/2004 | Friedman et al. |
| 6,806,122 B2 | 10/2004 | Oggioni et al. |
| 6,846,985 B2 | 1/2005 | Wang et al. |
| 6,846,994 B2 | 1/2005 | Wenner |
| 6,864,418 B2 | 3/2005 | Wang et al. |
| 6,891,110 B1 | 5/2005 | Pennaz et al. |
| 6,894,145 B2 | 5/2005 | Xiao et al. |
| 6,894,362 B2 | 5/2005 | Malik |
| 6,898,489 B1 | 5/2005 | Hayes, Sr. |
| 6,903,850 B2 | 6/2005 | Kay et al. |
| 6,916,968 B2 | 7/2005 | Shapira et al. |
| 6,933,848 B1 | 8/2005 | Stewart et al. |
| 6,940,408 B2 | 9/2005 | Ferguson et al. |
| 6,940,455 B2 | 9/2005 | Plettner |
| 6,956,283 B1 | 10/2005 | Peterson |
| 6,959,986 B2 | 11/2005 | Ushirogouchi et al. |
| 6,970,092 B2 | 11/2005 | Hum et al. |
| 6,980,865 B1 | 12/2005 | Wang et al. |
| 7,022,388 B2 | 4/2006 | Hashimoto et al. |
| 7,053,781 B1 | 5/2006 | Haire et al. |
| 7,061,523 B2 | 6/2006 | Fujita et al. |
| 7,071,830 B2 | 7/2006 | Sahlberg et al. |
| 2002/0092346 A1 | 7/2002 | Niekerk et al. |
| 2002/0092347 A1 | 7/2002 | Niekerk et al. |
| 2002/0130771 A1 | 9/2002 | Osborne et al. |
| 2002/0145525 A1 * | 10/2002 | Friedman et al. ......... 340/573.5 |
| 2004/0061655 A1 | 4/2004 | Forster et al. |
| 2005/0012616 A1 | 1/2005 | Forster et al. |
| 2005/0156744 A1 * | 7/2005 | Pires ................. 340/573.5 |
| 2005/0212660 A1 | 9/2005 | Hansen et al. |
| 2005/0230486 A1 | 10/2005 | Halope |
| 2005/0231371 A1 | 10/2005 | Rowe, Jr. |
| 2005/0242957 A1 | 11/2005 | Lindsay et al. |
| 2005/0285746 A1 | 12/2005 | Sengupta et al. |
| 2006/0290501 A1 | 12/2006 | Hammad et al. |
| 2010/0090802 A1 * | 4/2010 | Nilsson et al. ............... 340/10.1 |

FOREIGN PATENT DOCUMENTS

| | | |
|---|---|---|
| DE | 29813738 U1 | 1/1999 |
| DE | 19742126 A1 | 3/1999 |
| DE | 102004015994 A1 | 11/2005 |
| EP | 1459911 A1 | 9/2004 |
| EP | 1538556 A1 | 8/2005 |
| JP | 2004246816 A | 9/2004 |
| WO | 9614813 A1 | 5/1996 |
| WO | 9916019 A1 | 4/1999 |
| WO | 0180174 A1 | 10/2001 |
| WO | 2004016454 A1 | 2/2004 |
| WO | 2004025554 A1 | 3/2004 |
| WO | 2004046762 A1 | 6/2004 |
| WO | 2004074016 A1 | 9/2004 |
| WO | 2005006243 A2 | 1/2005 |
| WO | 2005070143 A2 | 8/2005 |
| WO | 2005076205 A1 | 8/2005 |
| WO | 2005089143 A2 | 9/2005 |
| WO | 2005109308 A1 | 11/2005 |

OTHER PUBLICATIONS

Doty, F. David, "High Resolution NMR Probes and RF Sample Coils for Liquids," Aug. 2001, Doty Scientific, Inc.

International Search Report for International Application No. PCT/US07/23303.

Written Opinion of the International Searching Authority for International Application No. PCT/US07/23303.

* cited by examiner

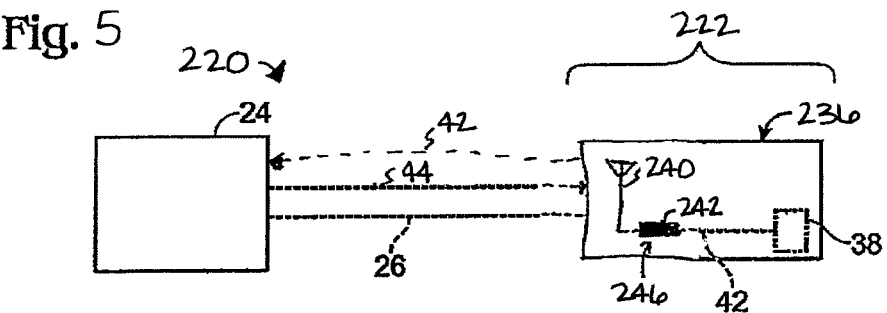
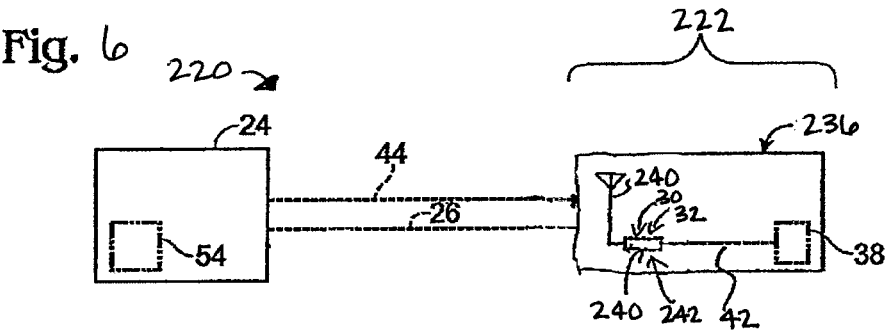
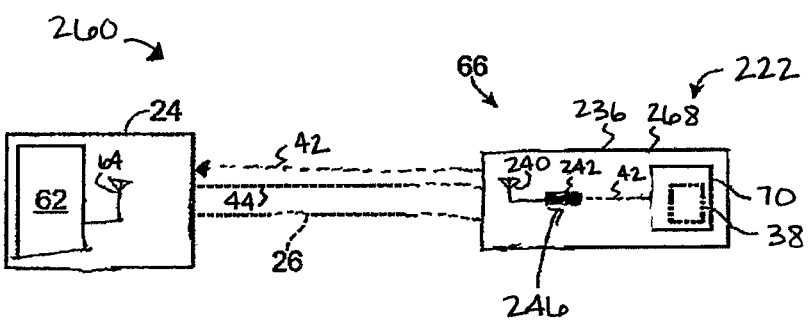
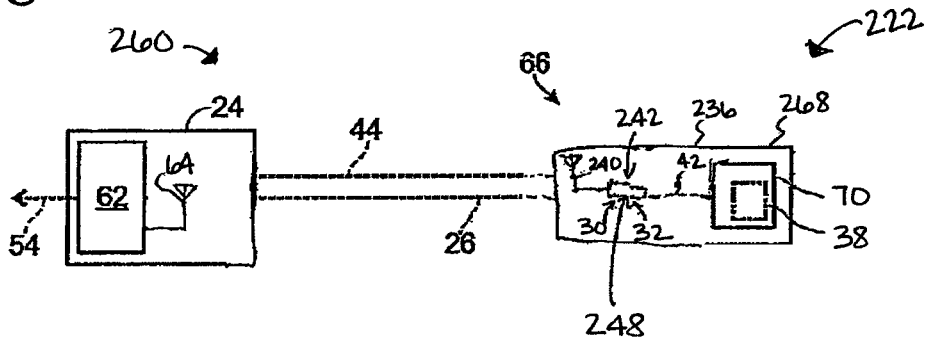

SENSORS AND SYSTEMS FOR DETECTING ENVIRONMENTAL CONDITIONS OR CHANGES

CROSS REFERENCE TO RELATED APPLICATIONS

This application is a continuation-in-part of U.S. patent application Ser. No. 12/902,115, filed Oct. 11, 2010, which is a continuation of U.S. patent application Ser. No. 11/615,313, filed Dec. 22, 2006 (now U.S. Pat. No. 7,812,731, issued Oct. 12, 2010). Each of these above-listed applications is hereby incorporated by reference.

BACKGROUND OF THE DISCLOSURE

The need to detect environmental conditions or changes arises in many situations. For example, solid materials or liquids may be introduced into or collect within an environment, parts or components of a system may wear down or out, or the temperature, pressure, chemical composition, atmosphere and/or some other environmental condition may change. Regardless of whether such changes or conditions may be beneficial, benign, harmful, desirable and/or undesirable, an indication of the change or condition may be useful. However, such changes or conditions may occur in locations where access is difficult or even impossible, where access, although possible or even simple, is undesirable for any number of reasons, and/or where the environmental conditions or changes may be hazardous to humans and/or equipment.

Nonexclusive illustrative examples of detecting such environmental conditions or changes may include detecting worn-out equipment or materials, detecting leaks in containers carrying a fluid, detecting the presence of fluids or vapors in undesirable locations, detecting injuries such as workplace or battlefield injuries, detecting leaching (leaks of chemicals) in silver or gold mining operations, detecting water or gas line bursts, or the like. Additional examples may include the detection of temperature changes, atmospheric changes (such as changes in pressure and/or composition), the presence or absence of one or more materials such as a chemical, and/or changes in other physical or environmental conditions such as light or noise levels, or wear of mechanical devices, such as brake pads or the like.

Additional nonexclusive illustrative examples of situations in which it would be desirable to detecting environmental conditions or changes arise in the field of health care. For example, the detection of body fluids would be desirable for assisting in the prevention of diaper rash, for potty training of infants, and in curing enuretic youngsters, as well as for detecting the leakage of blood or other fluids after surgery, invasive diagnostic procedures, or injury. As a further nonexclusive illustrative example, the detection of incontinence in chronically bedridden persons, such as in the elder care field, would be useful to facilitate better care for chronically bedridden persons.

For example, incontinence is a considerable problem in elder health care. Elders often are immobile, and if these immobile elders become incontinent and lose control of the evacuative functions of urination or defecation and soil themselves, they may be unable to help themselves or seek help. The urine or feces might stay in place long enough for the elder to develop sores, which can result in sickness, infection, and in the worse cases, even death.

The current method of determining whether an elder has lost control of his or her evacuative functions of urination or defecation requires a caregiver to manually check the elder's bedding and/or diaper. This is an arduous and demeaning process, both for the caregiver and for the elder. Thus, there exists a need for an easy and non-intrusive method of detecting incidents of incontinence in elders.

Examples of sensors or systems for detecting predetermined environmental conditions are disclosed in the following U.S. Pat. Nos. 5,557,263; 5,570,082; 5,904,671; 6,294,997; 6,373,395; 6,583,722; 6,774,800; 6,846,994; 6,916,968; 7,053,781; 7,071,830; and U.S. Patent Application Publication Nos. 2004/0061655; 2005/0012616; 2005/0285746. Examples of radio frequency identification (RFID) devices and systems are disclosed in the following U.S. Pat. Nos. 5,904,671; 6,294,997; 6,583,722; 6,774,800; 6,898,489; U.S. Patent Application Publication Nos. 2004/0061655; 2005/0012616; 2005/0285746; and in PCT Publication Nos. WO 99/16019; WO 01/80174; WO 2004/016454; WO 2004/046762; WO 2005/006243; WO 2005/025554; WO 2005/076205; WO 2005/109308. The complete disclosures of these and all other publications referenced herein are incorporated by reference in their entirety for all purposes.

SUMMARY OF THE DISCLOSURE

In one example, a system for detecting a predetermined environmental condition may include a circuit capable of providing information, a non-human interrogator device, and a shield. The interrogator device may be configured to read information provided by the circuit. The shield may have a first condition and a second condition. In the first condition the shield may be configured to preclude the interrogator device from reading information provided by the circuit. In the second condition the shield may be configured to enable the interrogator device to read information provided by the circuit. The shield may be configured to transition from the first condition to the second condition when the shield is exposed to the predetermined environmental condition.

In one example, a system for detecting a predetermined environmental condition may include a first device configured to transmit a first signal, a second device configured to receive a second signal, and a sensor. The sensor may include a third device and a shield disposed proximate the third device. The third device, responsive to receipt of the first signal by the third device, may be configured to transmit the second signal. The shield may be configured to preclude transmission of at least one of the first signal to the third device and the second signal from the third device. The efficacy of the shield may, upon exposure of the shield to the predetermined environmental condition, be sufficiently disrupted such that the disrupted shield may permit transmission of at least one of the first signal to the third device and the second signal from the third device.

In one example, a sensor for detecting a predetermined environmental condition may include a circuit capable of providing information and a shield disposed proximate the circuit. The shield may have a first condition and a second condition. In the first condition the shield may be configured to prevent access to information provided by the circuit. In the second condition the shield may be configured to permit access to information provided by the circuit. The shield may be configured to transition from the first condition to the second condition when the shield is exposed to the predetermined environmental condition.

In one example, a method of detecting a predetermined environmental condition may include providing a circuit capable of storing information, which may include predetermined information stored thereon, and a non-human interrogator device, which may be configured to read information stored on the circuit. The method may further include providing a shield. The shield may have a first condition and a second condition. In the first condition the shield may be configured to preclude the interrogator device from reading information stored on the circuit. In the second condition the shield may be configured to enable the interrogator device to read information stored on the circuit. The shield may be provided in the first condition, and the shield may be configured to transition from the first condition to the second condition when the shield is exposed to the predetermined environmental condition. The method may further include exposing the shield to the predetermined environmental condition such that the shield may transition from the first condition to the second condition; reading with the interrogator device the predetermined information stored on the circuit; and indicating that the predetermined environmental condition exists in response to the interrogator device reading the predetermined information stored on the circuit.

In one example, a system for detecting a predetermined environmental condition may include a circuit capable of selectively providing information and a non-human interrogator device. The circuit may include a reconfigurable antenna which, in a first condition, is configured to enable communications between the circuit and the interrogator device and, in a second condition, is configured to prevent communications between the circuit and the interrogator device. The reconfigurable antenna may be configured to transition from first conditions to second conditions upon exposure to the predetermined environmental condition or change.

In one example, a system for detecting a predetermined environmental condition may include a first device configured to transmit a first signal, a second device configured to receive a second signal, and a sensor. The sensor may include a third device having a reconfigurable antenna. The third device, responsive to receipt of the first signal by the third device, may be configured to selectively transmit the second signal. The reconfigurable antenna may be configured to preclude reception of the first signal by the third device and/or transmission of the second signal from the third device. A condition of the reconfigurable antenna may change, upon exposure of the third device to the predetermined environmental condition. For example, the changed condition may include disconnection of antenna elements from transmission and/or reception circuitry of the third device.

In one example, a sensor for detecting a predetermined environmental condition may include a transceiver circuit and a reconfigurable antenna. In a first condition, the reconfigurable antenna may have a first number of elements coupled to the transceiver circuit. In a second condition, the reconfigurable antenna may have a either a second number of elements coupled to the transceiver circuit or no elements coupled to the transceiver circuit. The reconfigurable antenna may be configured to transition from first condition to the second condition upon exposure to a predetermined environmental condition or change In one example, a method of detecting a predetermined environmental condition may include a providing sensor including a circuit capable of storing information, which may include predetermined information stored thereon and one or more antenna elements selectively attached to the circuit. In a first condition a first number of antenna elements are coupled to the circuit. In the second condition, at least one of the antenna elements is disconnected from the circuit. The sensor may be provided in the first condition, and be configured to transition from the first condition to the second condition upon exposure to the predetermined environmental condition. The method may further include exposing the sensor to the predetermined environmental condition such that the sensor transitions from the first condition to the second condition; reading with an interrogator device the predetermined information stored on the sensor; and indicating that the predetermined environmental condition exists in response to the interrogator device reading the predetermined information stored on the sensor.

BRIEF DESCRIPTION OF THE DRAWINGS

FIG. 5 is a schematic view of an illustrative example of a system, with a reconfigurable antenna shown in a first or conducting condition, for detecting environmental conditions or changes.

FIG. 6 is a schematic view of the system of FIG. 5, with the reconfigurable antenna shown in a second or non-conducting/disrupted condition.

FIG. 7 is a schematic view of an illustrative example of an RFID-based system, with a reconfigurable antenna shown in a first or conducting condition, for detecting environmental conditions or changes.

FIG. 8 is a schematic view of the RFID-based system of FIG. 7, with the reconfigurable antenna shown in a second or non-conducting/disrupted condition.

DETAILED DESCRIPTION

The following description provides specific details for a thorough understanding of, and enabling description for, various examples of the technology. One skilled in the art will understand that the technology may be practiced without many of these details. In some instances, well-known structures and functions have not been shown or described in detail to avoid unnecessarily obscuring the description of the examples of the technology. It is intended that the terminology used in the description presented below be interpreted in its broadest reasonable manner, even though it is being used in conjunction with a detailed description of certain examples of the technology. Although certain terms may be emphasized below, any terminology intended to be interpreted in any restricted manner will be overtly and specifically defined as such in this Detailed Description section. Any headings used herein are provided for ease of reading and are not intended to limit the disclosure in any way.

Illustrative Systems

Figure 1:
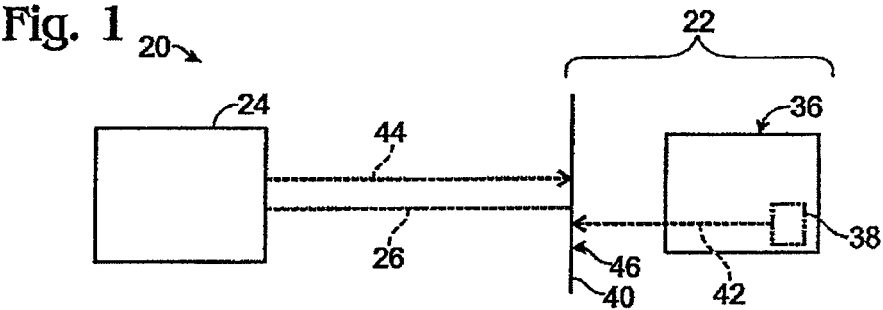
FIG. 1 is a schematic view of an illustrative example of a system for detecting environmental conditions or changes, with the shield shown in a first or shielding condition.
Figure 2:
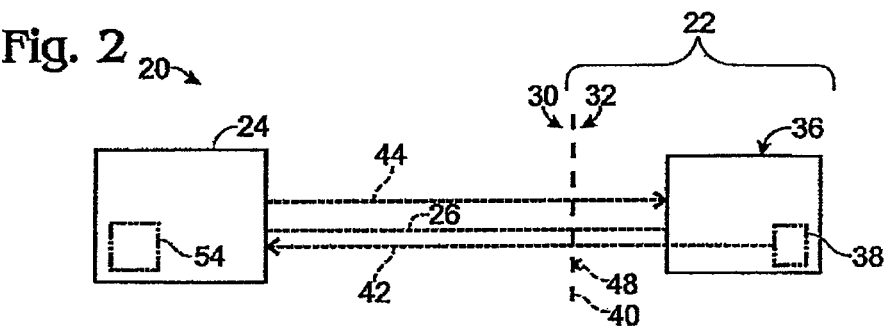
FIG. 2 is a schematic view of the system of FIG. 1, with the shield shown in a second or disrupted condition.

A nonexclusive illustrative example of a system 20 for detecting environmental conditions or changes is shown in FIGS. 1 and 2. As shown in the embodiments of FIGS. 1 and 2, sensor 22 includes shield 40, as discussed in greater detail below. Unless otherwise specified, system 20 and its various components may, but are not required to, contain at least one of the structure, components, functionality, and/or variations as the other systems for detecting environmental conditions or changes described and/or illustrated herein. As shown in the nonexclusive illustrative example presented in FIGS. 1 and 2, system 20 includes a sensor 22, a corresponding nonhuman reader or interrogator device 24, and a communication path 26 extending between the sensor 22 and the interrogator device 24. When used in combination, sensor 22 and a corresponding appropriately configured interrogator device 24 provide a system suitable for detecting at least one predetermined environmental condition 30 or predetermined environmental change 32, as will be more fully described below.

Sensor 22 includes a circuit 36, which is capable of storing, representing, or providing information 38 in a machine readable format, and a shield 40, which may be disposed proximate circuit 36. In some nonexclusive illustrative examples, the information 38 that is represented or provided by circuit 36 may be stored in or on circuit 36. As used herein, the storage of information refers to any embodiment of data or information in and/or on a tangible object, whether intrinsically, actively or intentionally.

Shield 40 is configured to prevent access to the information 38 stored in or on, represented by or provided by circuit 36, such as by precluding interrogator device 24 from reading the information 38 that is stored in or on, represented by or provided by circuit 36. For example, shield 40 may at least partially disrupt, interfere with, or interrupt communication path 26, as shown in the schematically represented nonexclusive illustrative example presented in FIG. 1.

A corresponding interrogator device 24 for sensor 22 is one that is configured to read or otherwise access the information 38 that is stored in or on, represented by or provided by circuit 36 in a particular machine readable format. If there is a communications path 26 between interrogator device 24 and circuit 36, interrogator device 24 may read or otherwise access the information 38 stored in or on, represented by or provided by circuit 36 when interrogator device 24 receives a second or information signal 42 from circuit 36, such as in response to a first or interrogation signal 44. In some nonexclusive illustrative examples, information signal 42 may at least partially include at least a portion of the information 38 that is stored in or on, represented by or provided by circuit 36. In some nonexclusive illustrative examples, information signal 42 may at least partially include, or be based on or derived from, at least a portion of interrogation signal 44 that has been at least partially reflected or otherwise retransmitted from circuit 36. As shown schematically in the nonexclusive illustrative example presented in FIG. 2, interrogation signal 44 may be generated by interrogator device 24. However, in some nonexclusive illustrative examples the interrogation signal 44 may be generated externally from interrogator device 24.

Information 38 may be stored in or on, represented by or provided by circuit 36 in any suitable machine readable format. As used herein, machine readable format refers to any format, system, mechanism or manner of embodying, storing, representing or providing data or information in a form that can be accessed, read, sensed, interpreted or otherwise detected by the hardware and/or software of an appropriately configured machine and/or computer. The suitability of a particular machine readable format may be determined based on the nature and suitability of the potentially available communications paths 26 between sensor 22 and interrogator device 24. The nature and suitability of the available communications paths 26 may depend on such factors as the quantum of information stored in or on, represented by or provided by circuit 36, the environment in which circuit 36 is or is expected to be used, the physical proximity or distance between sensor 22 and interrogator device 24, or the like.

In some nonexclusive illustrative examples, when sensor 22 and interrogator device 24 are optically visible relative to each other such that there is an optical communication path 26 between sensor 22 and interrogator device 24, information 38 may be stored, represented or provided in an optically readable format such as a barcode or any suitable type of machine readable characters or indicia. In some nonexclusive illustrative examples, such as where physical obstructions preclude an optical communication path 26 between sensor 22 and interrogator device 24, a magnetic or electromagnetic communication path 26 may exist between sensor 22 and interrogator device 24. When a magnetic communication path 26 is used, information 38 may be stored in or on, represented by or provided by a magnetic label or marker and may be detected by an appropriate device such as a Hall effect sensor. When an electromagnetic communication path 26 is used, information may be stored in or on, represented by or provided by an RFID tag, the usage of which will be more fully discussed below. Other nonexclusive illustrative examples of a communication path 26 may be based on acoustics, such as the use of surface acoustic wave devices, or any other suitable mechanism or method that is capable of transmitting information. These and other nonexclusive illustrative examples of communication paths are discussed in Klaus Finkenzeller, RFID HANDBOOK (Rachel Waddington trans., 2d ed. 2003), the complete disclosure of which is incorporated by reference in its entirety for all purposes.

Information 38 may be any quantum of data that is configurable to provide an indication of a detected predetermined environmental condition 30 or predetermined environmental change 32. In some nonexclusive illustrative examples, information 38 may be as simple as a single bit of data, which is sufficient to provide an indication of the existence or absence of the particular predetermined environmental condition 30 or predetermined environmental change 32 that sensor 22 is configured to detect. For example, circuit 36 may provide information 38 in the form of a simple binary yes/no indication that circuit 36 is detectable or otherwise readable by interrogator device 24, which may correspond to the existence or absence of the particular predetermined environmental condition 30 or predetermined environmental change 32 that sensor 22 is configured to detect. In some nonexclusive illustrative examples, such as in some nonexclusive illustrative examples where information 38 is a simple binary yes/no indication that circuit 36 is detectable or otherwise readable by interrogator device 24, the information 38 may be limited to information indicating the existence of circuit 36. In some nonexclusive illustrative examples, such as where circuit 36 is capable of storing more than a single bit of information, information 38 may be sufficient to provide more than a simple indication of the existence or occurrence of a particular environmental condition or environmental change. For example, information 38 may include any suitable combination of information or data such as location, object or personal identification, details regarding the particular environmental condition or environmental change that exists or has occurred, timing information regarding the duration of the detected environmental condition, elapsed time since the occurrence of the environmental change, or the like.

As shown in the nonexclusive illustrative example presented in FIGS. 1 and 2, shield 40 may be in a shielding or first condition 46 or in a disrupted or second condition 48. When shield 40 is in the first condition 46, shield 40 is configured to prevent access to the information 38 stored in or on, represented by or provided by circuit 36, such as by precluding interrogator device 24 from reading or otherwise accessing the information 38 that is stored in or on, represented by or provided by circuit 36, such as by at least partially disrupting, interfering with, or interrupting communication path 26, as schematically shown in FIG. 1. For example, when shield 40 is in the first condition 46, shield 40 may at least partially preclude transmission of an interrogation signal 44 from interrogator device 24 to circuit 36 and/or shield 40 may at least partially preclude the transmission of an information signal 42, which may at least partially contain or represent the information 38 stored in or on, represented by or provided by the circuit 36, from circuit 36 to the interrogator device 24.

The method or mechanism by which shield 40 disrupts, interferes with, or interrupts communication path 26 varies with the nature of the communication path 26, the interrogation signal 44, and information signal 42. For example, if the information 38 stored in or on, represented by or provided by circuit 36 is optically readable by interrogator device 24, then shield 40 might be at least partially opaque to at least one of communication path 26, interrogation signal 44, and information signal 42 when shield 40 is in the first condition 46. If the information 38 stored in or on, represented by or provided by circuit 36 is magnetically readable by interrogator device 24, then shield 40 might be configured to at least partially oppose the magnetic field of the interrogation signal 44 generated by interrogator device 24. For example, shield 40 may include a metallic surface positioned adjacent circuit 36 such that the eddy currents induced in the metallic surface at least partially oppose the magnetic field of the interrogation signal 44. If the information 38 stored in or on, represented by or provided by circuit 36 is readable by interrogator device 24 via electromagnetic coupling between interrogator device 24 and circuit 36, then shield 40 may be configured to at least partially disrupt, interfere with, or interrupt the electromagnetic field generated by interrogator device 24, such as where shield 40 acts as a radio frequency (RF) shield when circuit 36 is an RFID transponder. The use and operational principles of RF shields are known, and will not be discussed in detail here.

When shield 40 is in the second condition 48, shield 40 is configured to permit access to the information 38 stored in or on, represented by or provided by circuit 36, such as by enabling or permitting interrogator device 24 to read or otherwise access the information 38 that is stored in or on, represented by or provided by circuit 36, such as by permitting communication path 26 to extend from interrogator device 24 to circuit 36, as schematically shown in FIG. 2. For example, when shield 40 is in the second condition 48, the efficacy of shield 40 is sufficiently disrupted such that the disrupted shield 40 permits transmission of the interrogation signal 44 from interrogator device 24 to circuit 36 and/or the disrupted shield 40 permits transmission of the information signal 42 and/or the information 38 stored in or on, represented by or provided by the circuit 36 from circuit 36 to the interrogator device 24.

System 20 detects environmental conditions or changes based on the transition of shield 40 between the first condition 46 and the second condition 48. In particular, as shown in the nonexclusive illustrative example presented in FIGS. 1 and 2, shield 40 is configured such that exposure to a predetermined environmental condition 30 or predetermined environmental change 32 sufficiently disrupts shield 40 such that shield 40 transitions from first condition 46 to second condition 48, which permits transmission of the interrogation signal 44 from interrogator device 24 to circuit 36 and transmission of the information signal 42 and/or the information 38 stored in or on, represented by or provided by the circuit 36 from circuit 36 to the interrogator device 24. If interrogator device 24 receives information signal 42 and/or information 38 from circuit 36, system 20 provides an indication 54 of the predetermined environmental condition 30 or predetermined environmental change 32. In some nonexclusive illustrative examples, the complexity of indication 54 may vary with the complexity of information 38 stored in or on, represented by or provided by circuit 36 as well as with the ability of interrogator device 24 to access information 38.

The particular predetermined environmental condition or change to which a particular sensor is responsive may be determined by selecting a shield that has a shielding efficacy that will be disrupted if the shield is exposed to a particular condition or change. As nonexclusive illustrative examples, a soluble shield may be used if it is desired to detect the presence of a particular solvent, a shield that degrades or otherwise changes properties at certain temperatures may be used if it is desired to detect a particular temperature, or a selectively positioned material having low mechanical durability may be used if it is desired to detect mechanical wear beyond a certain threshold. In some nonexclusive illustrative examples, a shield may be selected based on its nonresponsiveness to a particular predetermined environmental condition or change whose detection is not desired. For example, if it is desired to detect temperature variations, but not the presence of a solvent, an insoluble shield that degrades at certain temperatures may be used.

In some nonexclusive illustrative examples, disruption of the shielding efficacy of a particular shield 40 or shielding material if the shield 40 transitions from a first or shielding condition 46 to a second or disrupted condition 48 may not correspond to mechanical disruption or damage to the shield or shielding material. In such an example, only the particular physical property that corresponds to shielding efficacy needs to be disrupted or altered. As a nonexclusive illustrative example, shield 40 may include an environmentally responsive liquid crystal material that is capable of at least partially disrupting, interfering with, or interrupting communication path 26 if the liquid crystal material is exposed to a predetermined environmental condition 30 or predetermined environmental change 32. For example, where the information 38 stored in or on, represented by or provided by circuit 36 is optically readable by interrogator device 24, shield 40 might be an environmentally responsive liquid crystal material that transitions from an at least partially opaque condition to an at least partially transparent condition if shield 40 transitions from first condition 46 to second condition 48 upon exposure to predetermined environmental condition 30 or predetermined environmental change 32.

In some nonexclusive illustrative examples, system 20 may be configured to only provide an indication that sensor 22 has been exposed to predetermined environmental condition 30 or predetermined environmental change 32. For example, shield 40 may be configured such that exposure to predetermined environmental condition 30 or predetermined environmental change 32 irreversibly disrupts shield 40 such that shield 40 is permanently transitioned from first condition 46 to second condition 48. In such an example, sensor 22 may be considered a single-use sensor, which must be replaced after use, or circuit 36 may be provided with a new shield 40 such the sensor 22 is at least partially reusable.

In some nonexclusive illustrative examples, system 20 may be configured to provide an indication that sensor 22 has not been exposed to predetermined environmental condition 30 or predetermined environmental change 32. For example, system 20 may be configured to provide an indication that sensor 22 has not been exposed to predetermined environmental condition 30 or predetermined environmental change 32 if interrogator device 24 has not received information signal 42 and/or information 38 from circuit 36 because shield 40 has not transitioned from first condition 46 to second condition 48.

In some nonexclusive illustrative examples, system 20 may be configured to provide an indication that sensor 22 is not currently exposed to and/or has previously been exposed to predetermined environmental condition 30 or predetermined environmental change 32. For example, shield 40 may be configured to transition from second condition 48 to first condition 46 if shield 40 is no longer exposed to predetermined environmental condition 30 or predetermined environmental change 32, such as where shield 40 is configured to reversibly transition between first condition 46 and second condition 48. In such an example, system 20 may be configured to provide an indication that sensor 22 is not currently exposed to and/or has previously been exposed to predetermined environmental condition 30 or predetermined environmental change 32 if interrogator device 24 has previously received, but is not currently receiving, information signal 42 and/or information 38 from circuit 36, such as where the efficacy of shield 40 is at least partially restored if shield 40 is no longer exposed to predetermined environmental condition 30 or predetermined environmental change 32.

Figure 3:
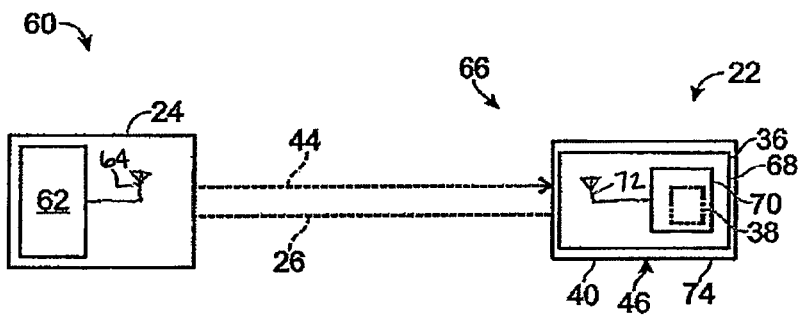
FIG. 3 is a schematic view of an illustrative example of an RFID-based system for detecting environmental conditions or changes, with the shield shown in a first or shielding condition.
Figure 4:
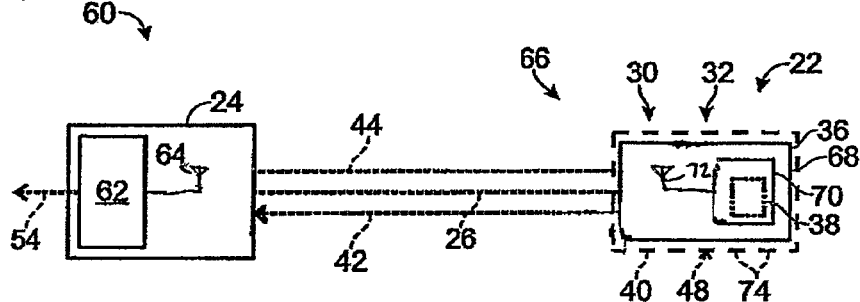
FIG. 4 is a schematic view of the RFID-based system of FIG. 3, with the shield shown in a second or disrupted condition.

A nonexclusive illustrative example of an RFID-based system 60 for detecting environmental conditions or changes is shown in FIGS. 3 and 4. Unless otherwise specified, system 60 and its various components may, but are not required to, contain at least one of the structure, components, functionality, and/or variations as the other systems for detecting environmental conditions or changes described and/or illustrated herein. As shown in the nonexclusive illustrative example presented in FIGS. 3 and 4, RFID-based system 60 may include an interrogator device 24, a corresponding sensor 22, and a shield 40, all of which are configured for use within an RFID-based system.

Nonexclusive illustrative examples of RFID technologies and systems that are suitable for use with the RFID-based system 60 may be classified based on the type of coupling and/or communication path 26 that exists between interrogator device 24 and transponder or circuit 36. Such nonexclusive illustrative examples may include inductive coupling, electromagnetic backscatter coupling, close coupling, electrical coupling, or the like. The use and operational principles of such RFID technologies and systems are known, and will not be discussed in detail here. Further discussion of RFID technologies and systems may be found in Klaus Finkenzeller, RFID HANDBOOK (Rachel Waddington trans., 2d ed. 2003), the complete disclosure of which is incorporated by reference in its entirety for all purposes.

As shown in the nonexclusive illustrative example presented in FIGS. 3 and 4, if used with an RFID-based system 60, interrogator device 24 includes an RFID reader 62 that is coupled to or includes an antenna 64. Antenna 64 is configured to transmit an interrogation signal 44, such as if the RFID reader 62 generates an electromagnetic field within an interrogation zone 66. In some nonexclusive illustrative examples, RFID reader 62 may continuously generate an electromagnetic field within interrogation zone 66. RFID reader 62 is also configured to receive a second or information signal 42, such as if an RFID-based sensor 22 is disposed within interrogation zone 66.

As shown in the nonexclusive illustrative example presented in FIGS. 3 and 4, if used with an RFID-based system 60, sensor 22 may include circuit 36, which may be included in the RFID transponder 68. Circuit 36 may include a data carrier 70, such as a microchip, which is coupled to a suitable coupling element 72, such as a coil or an antenna. In some nonexclusive illustrative examples, data carrier 70 may be conductively coupled to coupling element 72. When the shield 40 is in the second condition 48, RFID transponder 68 is configured to transmit information signal 42, and/or the information 38 that is stored in or on, represented by or provided by data carrier 70, to the RFID reader 62 of interrogator device 24 in response to RFID transponder 68 receiving an interrogation signal 44 from interrogator device 24. In some nonexclusive illustrative examples, information signal 42 may at least partially include, or be based on or derived from, at least a portion of interrogation signal 44 that has been at least partially reflected or otherwise retransmitted from circuit 36. For example, RFID transponder 68 may be configured to reflect back to the interrogator device 24 at least a portion of the electromagnetic field that corresponds to the interrogation signal 44. In some nonexclusive illustrative examples, an information signal 42 based on a reflected portion of interrogation signal 44 may provide a simple binary yes/no indication that circuit 36 is detectable or otherwise readable by interrogator device 24, which may correspond to the existence or absence of the particular predetermined environmental condition 30 or predetermined environmental change 32 that sensor 22 is configured to detect. In some nonexclusive illustrative examples, information signal 42 may at least partially carry information 38 in the form of a modulation imposed on a reflected portion of the interrogation signal 44, such as due to modulation of the reflection cross-section of RFID transponder 68. When RFID transponder 68 is passive, such as if RFID transponder 68 does not include its own power source, the interrogation signal 44 that is transmitted by interrogator device 24 may provide operating power to RFID transponder 68.

As shown in the nonexclusive illustrative example presented in FIG. 3, if used with an RFID-based system 60, shield 40 may be configured to preclude access to the information 38 stored in or on, represented by or provided by circuit 36 if shield 40 is in the first condition 46. For example, if shield 40 is in the first condition 46, shield 40 at least partially disrupts, interferes with, or interrupts RF-based communication path 26, which precludes interrogator device 24 from reading the information 38 that is stored in or on, represented by or provided by circuit 36, such as by precluding interrogator device 24 from transmitting interrogation signal 44 or power to sensor 22, by precluding sensor 22 from receiving interrogation signal 44 or power from interrogator device 24, and/or by precluding sensor 22 from transmitting information signal 42.

When used with an RFID-based system 60, shield 40 may include any material or configuration capable of at least partially disrupting, interfering with, or interrupting the RF-based communication path 26 that exists between interrogator device 24 and circuit 36, such as between antenna 64 and coupling element 72. For example, shield 40 may include a material capable of providing electromagnetic or RF shielding, such as a conductive material disposed between interrogator device 24 and circuit 36, such as where shield 40 includes a conductive material 74 that at least partially surrounds circuit 36 and/or coupling element 72. In some nonexclusive illustrative examples, conductive material 74 may at least partially form a Faraday cage around circuit 36 and/or coupling element 72. Nonexclusive illustrative examples of suitable conductive materials 74 include conductive sheets, conductive meshes, conductive greases, paints or ink, and the like. Nonexclusive illustrative examples of conductive sheets may include metal foils, such as gold or aluminum foils, carbon-based sheets, such as those based on carbon fibers, and the like. Nonexclusive illustrative examples of conductive meshes may include metallic meshes, carbon-based meshes, and the like.

A nonexclusive illustrative example of a system 220 for detecting environmental conditions or changes is shown in FIGS. 5 and 6. In contrast to sensor 22 of FIGS. 1 to 4, sensor 222 of FIGS. 5 and 6 includes antenna 240 having a soluble link 242, as discussed in greater detail below. Unless otherwise specified, system 220 and its various components may, but are not required to, contain at least one of the structure, components, functionality, and/or variations as the other systems for detecting environmental conditions or changes described and/or illustrated herein.

As shown in the nonexclusive illustrative example presented in FIGS. 5 and 6, system 220 includes a sensor 222, interrogator device 24, and a communication path 26 extending between the sensor 222 and the interrogator device 24. When used in combination, sensor 222 and a corresponding appropriately configured interrogator device 24 provide a system suitable for detecting at least one predetermined environmental condition 30 or predetermined environmental change 32, as is more fully described below.

Sensor 222 includes a circuit 236 and an antenna 240. Sensor 222 may also include soluble link 242 or soluble link 242 may be part of antenna 240. As one example, circuit 236 may be similar to circuit 36 of FIGS. 1 to 4. For example, circuit 236 may be capable of storing, representing, or providing information 38, and may be capable of communicating with interrogator device 24 via communication path 26. However, circuit 236 may differ from circuit 36 in certain ways. For example, circuit 236 is configured to interface with communication path 26 through antenna 240 via soluble link 242, whereas circuit 36 may include an integrated antenna 26 or other mechanisms for interfacing to communication path 26. Likewise, the interrogator device 24 of FIGS. 5 and 6 may be the same as or similar to the interrogator device 24 of FIGS. 1 and 2.

In sensor 222, antenna 240 is configured to transmit electromagnetic waves of any frequency from circuit 236 to communication path 26 via soluble link 242 and to provide electromagnetic waves of any frequency received from communication path 26 to circuit 236. For example, antenna 240 may be a stripline or coil antenna such as those discussed below with respect to FIGS. 16 to 19. However, dipole antennas, yagi antennas, directional antennas, omnidirectional antennas, wire antennas, single element antennas, multi-element antennas, and/or any other type of antenna suitable for given applications may be employed for those applications. Likewise, in embodiments of sensors configured to communicate though a non-radio frequency communication path 26, an acoustic transducer, optical transducer, magnetic transducer, and/or the like may be employed as or substituting for antenna 240. In such embodiments, electromagnets, Hall effect sensors, laser diodes, laser detectors, light emitting diodes, optical pickups, and/or surface acoustic wave devices are some examples of many elements that may be suitable employed as or substituting for antenna 240.

Also in sensor 222, soluble link 242 is configured to selectively couple circuit 236 and antenna 240. More specifically, soluble link 242 may be configured to selectively provide a conductive path between circuit 236 and antenna 240 and thus either enable access to the information 38 stored in or on, represented by or provided by circuit 236 from interrogator device 24 or preclude access to the information 38 from interrogator device 24. Stated another way, soluble link 242 may be configured to enable or disable communications between interrogator device 24 and circuit 236 depending on whether it is in a conductive or first condition, or in a non-conductive or second condition.

As shown in the nonexclusive illustrative example presented in FIGS. 5 and 6, soluble link 242 may be in a conducting or first condition 246 or in a non-conducting or second condition 248. When soluble link 242 is in the first condition 246, soluble link 242 is configured to provide a path between circuit 236 and antenna 240, e.g., to permit access to the information 38 stored in or on, represented by or provided by circuit 236, such as by enabling or permitting interrogator device 24 to read or otherwise access the information 38 that is stored in or on, represented by or provided by circuit 236, as schematically shown in FIG. 5. As one example, when soluble link 242 is in the first condition 246, soluble link 242 is configured to provide an electrical path between antenna 240 and transmission circuitry, reception circuitry, and/or a transceiver of circuitry 236.

For example, if soluble link 242 is in the first condition 246, soluble link 242 may be sufficiently conductive to provide an electrical connection between antenna 240 and circuit 236. Such a connection would permit electrical communications between antenna 240 and circuit 236 and hence facilitate transmission of the information signal 42 and/or the information 38 stored in or on, represented by or provided by the circuit 236 from circuit 236 to the interrogator device 24 and/or facilitate transmission of the interrogation signal 44 from interrogator device 24 to circuit 236.

However, if soluble link 242 is in the second condition 248, the soluble link is configured to disconnect antenna 240 from circuit 236. For example, soluble link 242 may cease to provide a conductive path between antenna 240 and circuit 236, may transition from a low resistance/impedance connection to a high resistance/impedance connection, electrically isolate antenna 240 from circuit 236, and/or the like. In system 220, such disconnection of antenna 240 from circuit 236 may function to prevent access to the information 38 stored in or on, represented by or provided by circuit 236, such as by precluding interrogator device 24 from reading or otherwise accessing the information 38 that is stored in or on, represented by or provided by circuit 236, as schematically shown in FIG. 6. For example, if soluble link 242 is in the second condition 248, soluble link 242 may at least partially preclude transmission of an interrogation signal 44 from interrogator device 24 to circuit 236 and/or soluble link 242 may at least partially preclude the transmission of an information signal 42, which may at least partially contain or represent the information 38 stored in or on, represented by or provided by the circuit 236, from circuit 236 to the interrogator device 24.

System 220 may detect environmental conditions or changes based on the transition of soluble link 242 between the first condition 246 and the second condition 248 of on the condition of soluble link 242 at a given time. In particular, as shown in the nonexclusive illustrative examples presented in FIGS. 5 and 6, soluble link 242 is configured such that exposure to a predetermined environmental condition 30 or predetermined environmental change 32 sufficiently disrupts soluble link 242 such that soluble link 242 transitions from first condition 246 to second condition 248, which permits transmission of the interrogation signal 44 from interrogator device 24 to circuit 236 and transmission of the information signal 42 and/or the information 38 stored in or on, represented by or provided by the circuit 236 from circuit 236 to the interrogator device 24. When interrogator device 24 receives information signal 42 and/or information 38 from circuit 236, interrogator device 24 provides an indication 54 of the predetermined environmental condition 30 or predetermined environmental change 32. In some nonexclusive illustrative examples, the complexity of indication 54 varies with the complexity of information 38 stored in or on, represented by or provided by circuit 236 as well as with the ability of interrogator device 24 to access information 38.

The particular predetermined environmental condition 30 or predetermined environmental change 32 to which a particular sensor is responsive may be determined by selecting a soluble link based on the type of condition or change that is to be detected. For example, a link soluble in a particular solvent (e.g., water, blood, sweat, urine, gasoline, etc.) may be used if it is desired to detect the presence of that particular solvent. However, a soluble link may also be selected based on its nonresponsiveness or resistance to change when exposed to predetermined environmental conditions or changes whose detection is not desired.

In these and other nonexclusive illustrative examples, the soluble link 242 may be configured such that exposure to predetermined environmental condition 30 or predetermined environmental change 32 irreversibly disrupts soluble link 242 such that soluble link 242 is permanently transitioned from first condition 246 to second condition 248 thus decoupling antenna 240 from circuit 236. In such an example, sensor 222 may be considered a single-use sensor, which must be replaced after use, or sensor 222 may be provided with a new soluble link 242 such the sensor 222 is at least partially reusable.

In some nonexclusive illustrative examples, system 220 may be configured to provide an indication that sensor 222 has not been exposed to predetermined environmental condition 30 or predetermined environmental change 32. For example, system 220 may be configured to provide an indication that sensor 222 has not been exposed to predetermined environmental condition 30 or predetermined environmental change 32 if interrogator device 24 receives information signal 42 and/or information 38 from circuit 236 because soluble link 242 has not transitioned from first condition 246 to second condition 248. Likewise, interrogator device 24 may be configured to communicate with circuit 236 while soluble link 242 is intact and to provide indication 54 to indicate a continuity of communication with circuit 236.

In other nonexclusive illustrative examples, system 220 may be configured to only provide an indication that sensor 222 has been exposed to predetermined environmental condition 30 or predetermined environmental change 32. For example, system 220 may be configured to provide an indication that sensor 222 has been exposed to predetermined environmental condition 30 or predetermined environmental change 32 if interrogator device 24 does not receive information signal 42 and/or information 38 from circuit 236 because soluble link 242 has transitioned from first condition 246 to second condition 248. More specifically, interrogator device 24 may be configured to communicate with circuit 236 while soluble link 242 is intact and to provide indication 54 based on a disruption of communications with circuit 236, such as upon a disintegration of soluble link 242.

A nonexclusive illustrative example of an RFID-based system 260 for detecting environmental conditions or changes is shown in FIGS. 7 and 8. As with sensor 222 of FIGS. 5 and 6, sensor 222 of FIGS. 7 and 8 includes antenna 240 having a soluble link 242. Unless otherwise specified, system 260 and its various components may, but are not required to, contain at least one of the structure, components, functionality, and/or variations as the other systems for detecting environmental conditions or changes described and/or illustrated herein. As shown in the nonexclusive illustrative example presented in FIGS. 7 and 8, RFID-based system 260 may include an interrogator device 24 and a corresponding sensor 222, all of which are configured for use within an RFID-based system.

As previously discussed with reference in the nonexclusive illustrative example presented in FIGS. 3 and 4, if used with an RFID-based system 60, interrogator device 24 includes an RFID reader 62 that is coupled to or includes an antenna 64 and is configured to generate an electromagnetic field within an interrogation zone 66.

As shown in the nonexclusive illustrative example presented in FIGS. 7 and 8, sensor 222 may include circuit 236, which may be included in the RFID transponder 268. Circuit 236 may also include a data carrier 70, such as a microchip, which is coupled to antenna 240 via soluble link 242. In some nonexclusive illustrative examples, data carrier 70 may be selectively and conductively coupled to antenna 240 via soluble link 242 to facilitate functionality such as discussed above with respect to preceding figures.

As shown in the nonexclusive illustrative example presented in FIG. 7, if used with an RFID-based system 60, soluble link 242 may be configured to, while in first condition 246, facilitate access to the information 38 stored in or on, represented by or provided by circuit 236, e.g., by providing a conductive path between circuit 236 and antenna 240 such that circuit 236 can communicate with interrogator device 24 via communication path 26.

As shown in the contrasting nonexclusive illustrative example presented in FIG. 8, soluble link 242 may transition to the second condition 248. Following such a transition, soluble link 242 would at least partially disrupt, interfere with, or interrupt conductivity between circuit 236 and antenna 240 thus interfering with circuit 236's ability to interface with communication path 26 and preclude interrogator device 24 from reading the information 38 that is stored in or on, represented by or provided by circuit 236. For example, with soluble link 242 in the second condition 248, circuit 236 would be unable to receive interrogation signal 44 or power from interrogator device 24, and would be unable to transmit information signal 42 to or otherwise communicate with interrogator device 24.

Although sensor 222 is described in conjunction with FIGS. 5 to 8 as having soluble link 242, other nonexclusive examples of sensors may employ other types of disruptable links instead of soluble link 242. For example, other disruptable links may be selected and/or employed based on the particular predetermined environmental condition or change to which a particular sensor is designed to detect. As nonexclusive illustrative examples, a disruptable link that degrades or otherwise changes properties at certain temperatures may be used if it is desired to detect a particular temperature, or a selectively positioned material having low mechanical durability may be used if it is desired to detect mechanical wear beyond a certain threshold. In some nonexclusive illustrative examples, a disruptable link may be selected based on its nonresponsiveness to a particular predetermined environmental condition or change whose detection is not desired. For example, if it is desired to detect temperature variations, but not the presence of a solvent, an insoluble disruptable link that degrades at certain temperatures may be used. Suitable nonexclusive examples of technologies for other types of disruptable links include the technologies discussed herein with respect to FIGS. 3, 4, and 9 to 15.

Illustrative Sensors

Schematic cross-sectional views of nonexclusive illustrative examples of sensors 22 and shields 40 are shown in FIGS. 9 to 15. Unless otherwise specified, each of the sensors 22 shown in FIGS. 9 to 15 may, but are not required to, contain at least one of the structure, components, functionality, and/or variations as the other sensors described and/or illustrated herein.

Figure 9:
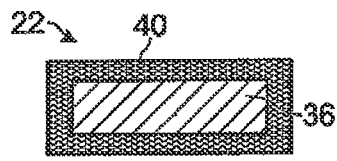
FIG. 9 is a schematic cross-sectional view of an illustrative example of a sensor that has separate shields.
Figure 10:
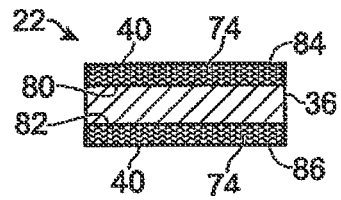
FIG. 10 is a schematic cross-sectional view of an illustrative example of a sensor that has a continuous shield.

As shown in the nonexclusive illustrative example presented in FIG. 9, shield 40 may completely surround circuit 36. For example, as discussed above, shield 40 may be in the form of a Faraday cage, such as where a conductive material 74 completely or nearly completely surrounds circuit 36.

In some nonexclusive illustrative examples, shield 40 may not completely surround circuit 36. For example, as shown in the nonexclusive illustrative example presented in FIG. 10, sensor 22 may include a circuit 36 that has first and second opposed major sides, faces or surfaces 80, 82. In such an example, shield 40 includes first and second portions 84, 86 of conductive material 74 that are disposed on the respective first and second opposed major sides, faces or surfaces 80, 82 of circuit 36.

In some nonexclusive illustrative examples, the predetermined environmental condition 30 or predetermined environmental change 32 that system 20 is configured to detect may include the presence of a predetermined fluid. In such an example, at least a portion of shield 40 exhibits a response if exposed to the fluid. For example, at least a portion of shield 40 may chemically respond if exposed to the fluid, such as where at least a portion of shield 40 is at least partially soluble or otherwise subject to breakdown if exposed to the predetermined fluid. Such an at least partially soluble shield 40 may be configured to at least partially transition from the first or shielding condition 46 to the second or disrupted condition 48 if shield 40 is exposed to the predetermined fluid. For example, at least a portion of an at least partially soluble shield may dissolve if the shield is exposed to the predetermined fluid, which may enable the transition of shield 40 from the first or shielding condition 46 to the second or disrupted condition 48, such as by sufficiently disrupting the efficacy of shield 40 such that there is a communication path 26 extending from interrogator device 24 to circuit 36, as suggested in FIG. 2. In some nonexclusive illustrative examples, at least a portion of shield 40 may otherwise respond if exposed to the predetermined fluid such as by hardening, swelling, or the like.

Figure 11:
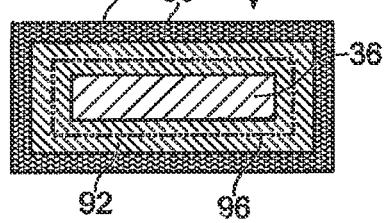
FIG. 11 is a schematic cross-sectional view of an illustrative example of a sensor that has a shield that includes a carrier.

In some nonexclusive illustrative examples, an at least partially soluble shield 40 may include a shielding layer 90 that is at least partially disposed on a carrier material 92, as shown in FIG. 11. The shielding layer 90 may be configured such that, if shield 40 is in the first condition 46, shielding layer 90 prevents access to the information 38 stored in or on, represented by or provided by circuit 36, such as by precluding interrogator device 24 from reading the information 38 that is stored in or on, represented by or provided by circuit 36, such as by at least partially disrupting, interfering with, or interrupting communication path 26, as schematically shown in FIG. 1. For example, if shield 40 is in the first condition 46, shielding layer 90 may at least partially preclude transmission of an interrogation signal 44 from interrogator device 24 to circuit 36 and/or shielding layer 90 may at least partially preclude the transmission of an information signal 42, which may at least partially contain or represent the information 38 stored in or on, represented by or provided by the circuit 36, from circuit 36 to the interrogator device 24.

The use of a carrier material may permit or simplify the use of particular shielding/conductive materials for shielding layer 90. For example, such as in the case of an RFID-based system, shielding layer 90 may be in the form of a conductive ink, grease or paint that is printed or otherwise deposited onto the carrier material 92. In such an example, the structural integrity of shield 40 may be provided by the carrier material 92 while the shielding efficacy may be provided by the shielding layer 90. Even though the shielding material itself may be relatively insoluble or otherwise unresponsive to the presence of the predetermined environmental condition 30, predetermined environmental change 32, or predetermined fluid to which shield 40 is exposed, the carrier material 92 may itself be at least partially soluble or otherwise subject to breakdown if so exposed. Thus, because the structural integrity of shield 40 is provided by the carrier material 92, the breakdown of carrier material 92 may at least partially disrupt shielding layer 90 and cause the transition of shield 40 from the first or shielding condition 46 to the second or disrupted condition 48 if shield 40 is exposed to predetermined environmental condition 30, predetermined environmental change 32, or the predetermined fluid.

When sensor 22 is configured for use in the detection of a water-based fluid, examples of suitable materials for carrier material 92 may include a water-soluble polymer such as polyvinyl alcohol (PVA). Other water-soluble materials such as soluble rice paper or the like may also be used.

In some nonexclusive illustrative examples, the at least partially soluble shield 40 of sensor 22 may be configured such that its solubility is at least partially temperature dependent. For example, the water solubility of a water-soluble carrier material 92 may be changed by changing the molecular weight of a polymer utilized in the carrier material, such as by controlling crosslinking of the polymer. By increasing crosslinking of the polymer by a suitable amount, such as by a several-fold increase in molecular weight, the water-soluble material may become substantially insoluble in cold water, but still may remain soluble in hot water.

In some nonexclusive illustrative examples where an RFID-based system 60 is configured to detect the presence of a predetermined fluid, shielding layer 90 may include a conductive material that has its conductivity characteristics altered by exposure to a predetermined substance or chemical. For example, shielding layer 90 may include a conductive material whose conductance is reduced or eliminated if the conductive material is exposed to a predetermined fluid such as water or a fluid that is discharged during an incontinence event, such as urine.

In addition to use with at least partially soluble shields, a shielding layer 90 may be used in sensors configured to detect mechanical changes. As a nonexclusive illustrative example, a shielding layer 90, such as a metal foil in the case of an RFID-based system 60, may be selectively placed within a component that is subject to mechanical wear or chemically induced reductions to structural volume. A nonexclusive illustrative example of such use of a shielding layer 90 would be the inclusion of sensor 22 within a friction-inducing component, such as one tending to decrease in thickness during use, such as a brake pad. By placing sensor 22 at a predetermined depth in such a component, wear of the component to the predetermined depth will expose the shielding layer 90 of the sensor to wear. In such an example, use of a shielding layer 90 that has little resistance to wear, such as a metal foil in the case of an RFID-based system 60, will cause the shield 40 to quickly transition from the first condition 46 to the second condition 48 such that the system 60 will detect the wear of the component to the predetermined depth.

In some nonexclusive illustrative examples, sensor 22 may include a facilitator 96 configured to at least partially ensure, stimulate, accelerate or otherwise enable the transition of shield 40 from the first or shielding condition 46 to the second or disrupted condition 48 if sensor 22 and/or shield 40 is exposed to predetermined environmental condition 30 or the predetermined environmental change 32. Unless otherwise specified, each of the facilitators 96 described herein may, but are not required to, contain at least one of the structure, components, functionality, and/or variations as the other facilitators described and/or illustrated herein. The facilitator 96 may be any material, structure, or mechanism capable of at least partially enabling the transition of shield 40 from the first or shielding condition 46 to the second or disrupted condition 48 if sensor 22 and/or shield 40 is exposed to the predetermined environmental condition 30 or the predetermined environmental change 32. For example, by expanding, contracting, and/or mechanically or chemically interacting with the environment, facilitator 96 may enable the transition of shield 40 from the first or shielding condition 46 to the second or disrupted condition 48, such as by sufficiently disrupting the efficacy of shield 40 such that a communication path 26 is enabled from interrogator device 24 to circuit 36, as suggested in FIG. 2. Nonexclusive illustrative examples of mechanisms by which facilitator 96 may mechanically or chemically interact with the environment may include melting, swelling, charring, dissolving, or otherwise decomposing. In some nonexclusive illustrative examples, facilitator 96 may be configured to ensure the transition of shield 40 from the first or shielding condition 46 to the second or disrupted condition 48 if sensor 22 and/or shield 40 is exposed to the predetermined environmental condition 30 or the predetermined environmental change 32.

In some nonexclusive illustrative examples, the facilitator 96 may be at least partially enclosed by, or integral with, the shielding layer 90 and/or carrier material 92. For example, as suggested in the nonexclusive illustrative example presented in FIG. 11, facilitator 96 may be at least partially disposed within, or be a part of, carrier material 92. In such examples, facilitator 96 may be at least partially formed from a material that is non-shielding relative to circuit 36. For example, if sensor 22 is used in an RFID-based system 60, facilitator 96 may be fabricated from a suitable non-conducting material such as a plastic, a glass, a ceramic, or the like.

In some nonexclusive illustrative examples, facilitator 96 may be configured to expand or increase in volume if sensor 22 is exposed to predetermined environmental condition 30 or predetermined environmental change 32. For example, facilitator 96 may be configured to expand or increase in volume if shield 40 is exposed to a predetermined fluid. In some nonexclusive illustrative examples, facilitator 96 may include a carrier material 92 that at least partially encloses circuit 36, with shielding layer 90 enclosing at least a portion of circuit 36 and at least a portion of facilitator 96. A facilitator 96 that is configured to expand or increase in volume if sensor 22 is exposed to predetermined environmental condition 30 or the predetermined environmental change 32 may be distinct from but within or enclosed by carrier material 92, or the carrier material 92 may itself be configured to expand or increase in volume if it is exposed to predetermined environmental condition 30 or the predetermined environmental change 32.

Figure 12:
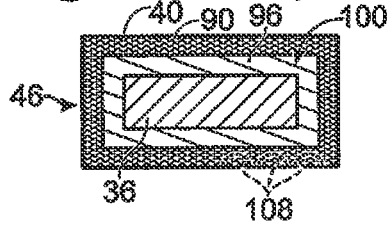
FIG. 12 is a schematic cross-sectional view of an illustrative example of a sensor that has an expanding facilitator, with the shield shown in a first or shielding condition.
Figure 13:
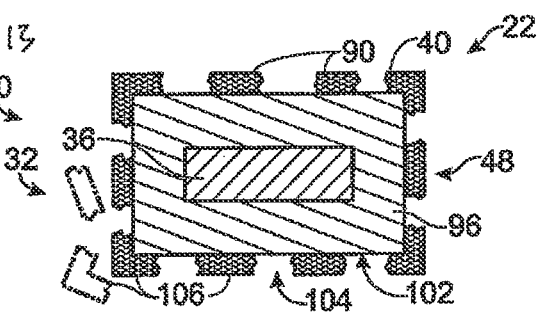
FIG. 13 is a schematic cross-sectional view of the sensor of FIG. 12, with the shield shown in a second or disrupted condition.

As shown in the nonexclusive illustrative example presented in FIGS. 12 and 13, at least a portion of shield 40, such as at least a portion of shielding layer 90, including any associated carrier material 92, may enclose a facilitator 96 that is configured to expand or increase in volume if sensor 22 is exposed to predetermined environmental condition 30 or predetermined environmental change 32. In such an example, if facilitator 96 is in a first or unexpanded condition 100, shielding layer 90 is sufficiently intact such that shield 40 is in the first or shielding condition 46, as shown in FIG. 12. When sensor 22 and/or facilitator 96 are exposed to predetermined environmental condition 30 or predetermined environmental change 32, such as to a predetermined fluid, facilitator 96 increases in volume and transitions from first condition 100 to a second or expanded condition 102, as shown in FIG. 13. The increase in volume of facilitator 96 if it is exposed to the predetermined environmental condition or change induces stresses in the shielding layer 90 that are sufficient to at least partially disrupt or rupture the shielding layer 90, such as by formation of gaps 104 in the shielding layer 90, which may cause the transition of shield 40 from the first or shielding condition 46 to the second or disrupted condition 48. The presence of gaps 104 in the shielding layer 90 may alone be sufficient to cause the transition of shield 40 from the first or shielding condition 46 to the second or disrupted condition 48. However, in some nonexclusive illustrative examples, the transition of shield 40 from the first or shielding condition 46 to the second or disrupted condition 48 may occur if the fragments 106 of the shielding layer 90 slough off or otherwise separate from sensor 22, as indicated in FIG. 13. In some nonexclusive illustrative examples, environmental conditions may assist or enhance the separation of fragments 106 from sensor 22. For example, fluid flow, which may be turbulent, proximate sensor 22 may assist or enhance the separation of fragments 106 from sensor 22.

Nonexclusive illustrative examples of suitable materials for a facilitator 96 that is configured to expand or increase in volume if sensor 22 is exposed to predetermined environmental condition 30 or the predetermined environmental change 32 include those materials that provide an expansion large enough to induces stresses in the shielding layer 90 that are sufficient to at least partially disrupt or rupture the shielding layer 90. For example, if used with a sensor 22 configured to detect the presence of a fluid, facilitator may be in the form of a compressed sponge or other material or object tending to expand in response to absorption of the fluid. For example, facilitator 96 may be an absorbent polymer, such as a high-gelling capacity crosslinked salt of polyacrylic acid, such as sodium polyacrylate, which is a crosslinked acrylic acid polymersodium salt.

In some nonexclusive illustrative examples of sensor 22, facilitator 96 may be configured to expand or increase in volume based on a chemical reaction. For example, facilitator 96 may be configured to undergo a chemical reaction if sensor 22 and/or facilitator 96 are exposed to the predetermined environmental condition 30 or the predetermined environmental change 32. Such a chemical reaction may be one that expansively produces a gas. For example, if used with a sensor 22 configured to detect the presence of a fluid, facilitator 96 may be configured to react with the fluid in a chemical reaction that produces a gaseous product. For example, facilitator 96 may include a mixture of citric acid and sodium bicarbonate, which react vigorously to produce carbon dioxide if mixed in a fluid such as water.

In some nonexclusive illustrative examples of sensor 22, such as where sensor 22 includes an expanding facilitator 96 as described above, shielding layer 90 may include at least one stress enhancer 108, as indicated in FIG. 12. In such an example, shield 40 is configured such that at least one stress enhancer 108 induces stress concentrations within the shielding layer 90 if the expanding facilitator 96 increases in volume. Such stress concentrations within the shielding layer 90 may be sufficient to at least partially enable rupture of the shielding layer 90 and enable the transition of shield 40 from the first or shielding condition 46 to the second or disrupted condition 48. For example, as indicated in FIG. 12, at least one stress enhancer 108 may be provided on shielding layer 90 in the form of regions of reduced thickness. Such regions of reduced thickness will lead to locally higher tensile stresses if the shielding layer is stretched over the expanded facilitator 96 if the facilitator is in the second or expanded condition.

In some nonexclusive illustrative examples, facilitator 96 may be configured to mechanically ensure the disruption of shielding layer 90 if sensor 22 and/or shield 40 are exposed to predetermined environmental condition 30 or the predetermined environmental change 32. For example, as schematically represented in the nonexclusive illustrative example presented in FIGS. 14 and 15, facilitator 96 may include a plurality of ridges or projections 112. Ridges or projections 112 may be formed in any suitable pattern. For example, ridges or projections 112 may include a series of two-dimensional projections in the form of linear or curvilinear ridges, which may intersect and/or be parallel. Ridges or projections 112 may alternately or additionally include an array or other distribution of a series of generally one-dimensional projections such as generally pyramidal or conical shapes. Ridges or projections 112 may be at least partially formed from a material that is non-shielding relative to circuit 36. For example, if sensor 22 is used in an RFID-based system 60, the ridges or projections 112 may be fabricated from a suitable non-conducting material such as a plastic, a glass, a ceramic, or the like.

Figure 14:
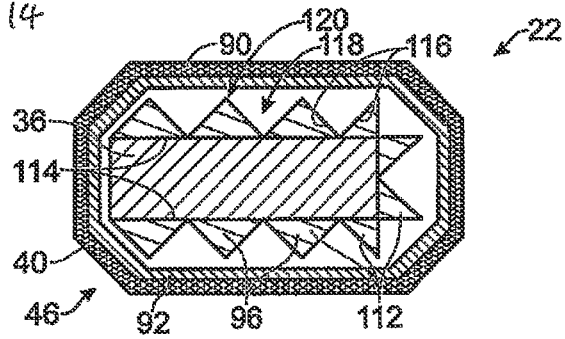
FIG. 14 is a schematic cross-sectional view of an illustrative example of a sensor that has a differential surface area based facilitator, with the shield shown in a first or shielding condition.

A facilitator 96 that includes a plurality of ridges or projections 112, may be used with a shield 40 that has a shielding layer 90 deposited on a carrier material 92, such as where shielding layer 90 includes a conductive ink or the like printed onto carrier material 92, as schematically represented in FIG. 14. As discussed above, the structural integrity of such a shield may be provided by the carrier material 92 while the shielding efficacy may be provided by the shielding layer 90. For example, the thicknesses of shielding layer 90 may be significantly larger than the thickness of carrier material 92. By way of nonexclusive illustrative example, carrier material 92 may have a thickness of approximately 0.003 inches (76 μm) while shielding layer 90 may have a thickness of approximately 0.0005 inches (12 μm).

Figure 15:
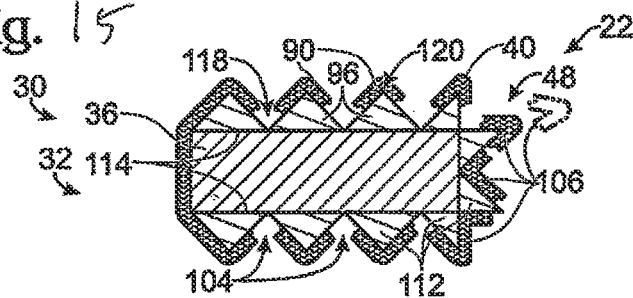
FIG. 15 is a schematic cross-sectional view of the sensor of FIG. 14, with the shield shown in a second or disrupted condition.

Although the at least partial dissolution or breakdown of carrier material 92 may disrupt shielding layer 90 to a sufficient extent as to cause shield 40 to transition from the first or shielding condition 46 to the second or disrupted condition 48 if shield 40 is exposed to predetermined environmental condition 30 or predetermined environmental change 32, the inclusion of a facilitator 96 that includes a plurality of ridges or projections 112 may ensure that shielding layer 90 is sufficiently disrupted to transition shield 40 to the second or disrupted condition 48. In particular, the plurality of ridges or projections 112 may prevent shielding layer 90 from depositing or decaling itself onto the surfaces 114 of circuit 36 subsequent to the dissolution or breakdown of carrier material 92. As may be observed from the schematic representation of the nonexclusive illustrative example presented in FIG. 14, the surface area of the exterior surfaces 116 of the plurality of ridges or projections 112 is significantly larger than the surface area of the shielding layer 90 due to the fact that shielding layer 90 passes across the valleys 118 between the ridges or projections 112. Thus, in the event that shielding layer 90 tends to deposit or decal itself onto the plurality of ridges or projections 112 upon the dissolution or breakdown of carrier material 92, shielding layer 90 may be disrupted into fragments 106 that are separated by gaps 104. Shielding layer 90 may be disrupted into fragments 106 because shielding layer 90 lacks sufficient material to deposit or decal itself over the entirety of the surfaces 116 of the peaks 120 and valleys 118 of the ridges or projections 112 without rupturing, as schematically represented in FIG. 15. By way of nonexclusive illustrative example, the depths of the valleys 118 between the ridges or projections 112 may be approximately 0.063 inches (1.6 mm or 1600 μm).

Schematic plan views of nonexclusive illustrative examples of antennas 240 and soluble links 242 are shown in FIGS. 16 to 19. Unless otherwise specified, each of the antennas 240 and soluble links 242 shown in FIGS. 16 to 19 may, but are not required to, contain at least one of the structure, components, functionality, and/or variations as the other sensors described and/or illustrated herein.

Figure 16:
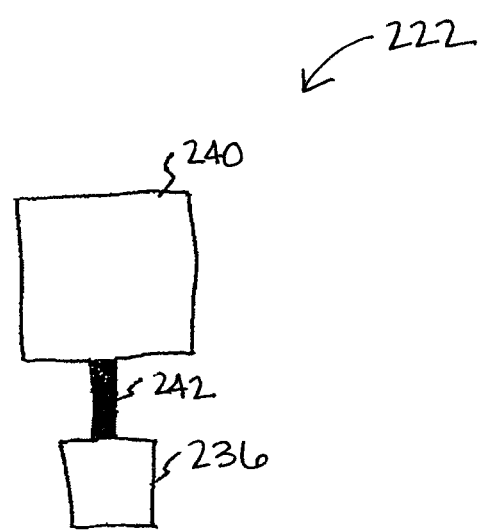
FIG. 16 is a schematic plan view of an illustrative example of a sensor having a disconnectable single element stripline patch antenna with a soluble link shown in a first or conducting condition.
Figure 17:
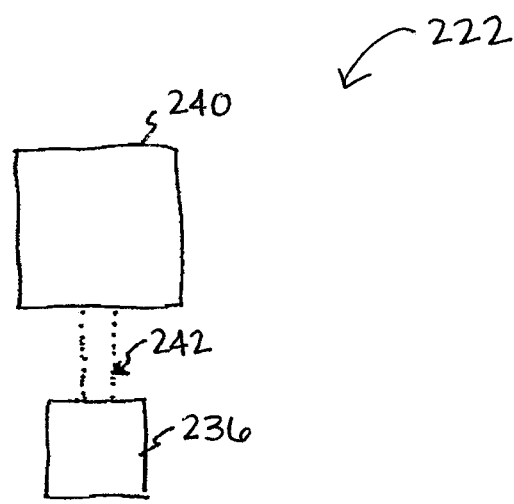
FIG. 17 is a schematic plan view of the sensor of FIG. 16, with the soluble link shown in a second or non-conducting/disrupted condition.

Shown in the nonexclusive illustrative example presented in FIGS. 16 and 17 are plan views of an illustrative example of a sensor 222 having a disconnectable single element stripline patch antenna 240 coupled to circuit 236 via soluble link 242. As discussed above, e.g., with respect to FIGS. 5 to 8, sensor 222 is configured to communicate with an interrogator device 24 if soluble link 24 is in a first condition, as shown in FIG. 16, and which cannot communicate with interrogator device 24 upon occurrence of a predetermined environmental condition 30 or predetermined environmental change 32 that causes disruption of soluble link 242, as illustrated by FIG. 17.

As shown in the nonexclusive illustrative example of FIGS. 16 and 17, antenna 240 is a stripline patch antenna, which may have any suitable dimensions, geometry, shape, and/or the like. Although illustrated as a substantially square and edge-fed antenna, antenna 240 could, for example, be shaped as non-square polygon or as a continuous curve. Likewise, antenna 240 may be fed from any suitable location and may have or omit a return coupling to circuit 236.

As discussed above, soluble link 242 may be configured such that exposure to predetermined environmental condition 30 or predetermined environmental change 32 irreversibly disrupts soluble link 242 such that soluble link 242 is permanently transitioned from first condition 246 to second condition 248 thus decoupling antenna 240 from circuit 236. As one example, disruption of soluble link 242 transitions soluble link 242 from a conductive condition to a non-conductive condition. Also, in the illustrated example, a single "near connector" soluble link 242 is employed to selectively couple antenna 240 to circuit 236. For example, such a near connector soluble link 242 may be positioned at or near circuit 236 such that there is minimal or no radiating antenna element connected to circuit 236 after disruption of soluble link 242.

Soluble link 242 may include or be formed of any suitable configuration of materials such as conductive materials, carrier materials, facilitators, and/or the like. In some nonexclusive illustrative examples, conductive materials are employed in conjunction with carrier materials to provide an electrically conductive link between circuit 236 and antenna 240 which may be disrupted or otherwise disintegrated upon contact or other exposure to a predetermined solvent. Such examples may be employed with or without use of facilitators which may configured to at least partially ensure, stimulate, accelerate or otherwise enable disintegration of soluble link 242. Some examples of suitable conductive materials, carrier materials, and facilitators are discussed with respect to FIGS. 3, 4, and 9 to 15. In yet other nonexclusive illustrative examples, a portion, a substantial portion, or an entirety of the antenna may itself be soluble. In such examples, the antenna may be formed of conductive materials, carrier materials, facilitators, and/or the like. Upon contact or other exposure to predetermined environmental condition 30 or predetermined environmental change 32, the portion, substantial portion, or entirety of the antenna would disintegrate and disrupt the circuit 236's ability to interface to communication path 26.

While FIGS. 16 and 17 illustrate a nonexclusive illustrative example of a sensor having a single soluble link, in yet other nonexclusive illustrative examples, multiple soluble links may be employed. For example, multiple soluble links may be employed such that in a first condition, circuit 236 is effectively coupled to an antenna having certain characteristics (e.g., shape, number of elements, frequency response, resonant frequency, radiation pattern, gain, impedance, strip length, coupled inductive elements, etc.). In a second condition, one or more of the soluble links may disintegrate leaving circuit 236 effectively coupled to an antenna having at least one changed characteristic. In conjunction with at least one example of such a sensor, interrogator device 24 may be configured to detect the changed antenna characteristic, for example, by transmitting an interrogation signal and detecting a reflected frequency that differs based on whether one or more of the soluble links have been disrupted.

Figure 18:
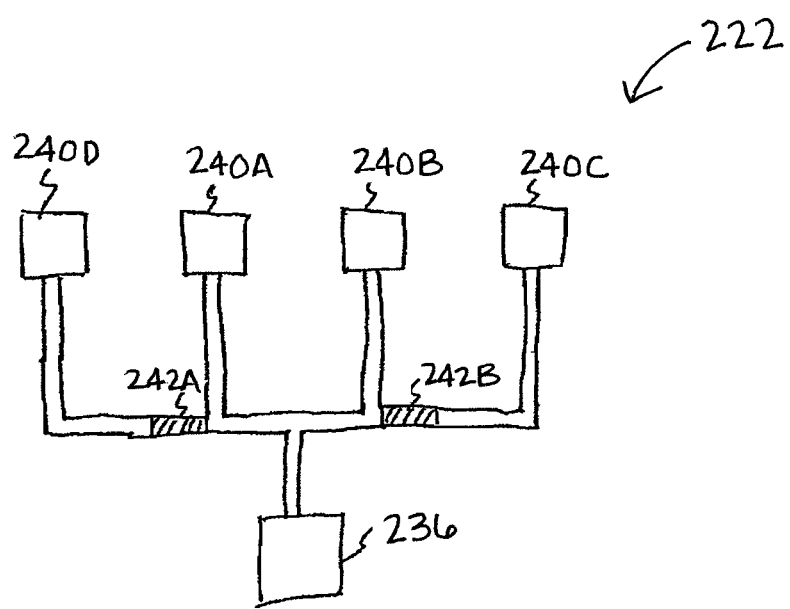
FIG. 18 is a schematic plan view of an illustrative example of a sensor having a disconnectable stripline patch antenna.

Shown in the nonexclusive illustrative example presented in FIG. 18 is a schematic plan view of an illustrative example of a sensor having a tunable multi-element patch antenna that has multiple soluble links. In the nonexclusive illustrative example of FIG. 18, sensor 242 includes circuit 236 and a multi-element antenna having elements 240A-240D. The multi-element antenna also includes soluble links 242A and 242B. In this nonexclusive illustrative example while sensor 222 is in a first condition, all of elements 240A-240D are coupled to circuit 236. Further, soluble links 242A and 242B are configured to disconnect elements 240C and 240D from circuit 236 and from elements 240A and 240B upon occurrence of a predetermined environmental condition 30 or predetermined environmental change 32.

Figure 19:
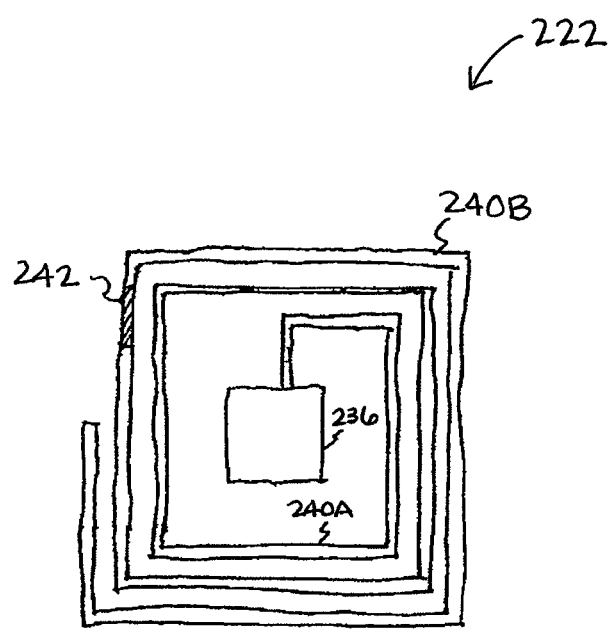
FIG. 19 is a schematic plan view of an illustrative example of a sensor having a tunable coil antenna.

Shown in the nonexclusive illustrative example presented in FIG. 19 is a schematic plan view of an illustrative example of a sensor having a tunable coil antenna. In the nonexclusive illustrative example of FIG. 19, sensor 242 includes circuit 236, antenna portions 240A and 240B, and soluble link 242. In this nonexclusive illustrative example while sensor 222 is in a first condition, soluble link 242 functions to couple antenna portion 240B to antenna portion 240A. As shown in FIG. 19, soluble link 242 is configured to be disrupted upon occurrence of a predetermined environmental condition 30 or predetermined environmental change 32, thus disconnecting antenna portion 240B, changing the effective number of antenna loops coupled to circuit 236, and changing/tuning an operating characteristic of the antenna, such as its frequency response, gain, or resonant frequency. Although specific nonexclusive examples of certain tuneable antennas are illustrated in FIGS. 18 and 19, other tunable antennas may be suitably employed. For example, a soluble link may be configured to reshape a stripline antenna, to bypass a portion of an antenna, to provide an alternate feed or return connection to circuit 236, and/or the like.

Illustrative Applications

Nonexclusive illustrative examples of applications of/for the technology described herein are now provided. It is understood that while the technology and use thereof is described in varying levels of detail with respect to the various described applications, the provided examples are not intended to be an exhaustive list of all possible applications in which the technology may be suitably employed.

As nonexclusive illustrative examples, and as alluded to above, the technology may be employed in a wide range of applications in any number of fields. For example, aspects of the technology may be employed in military, law enforcement, construction, or industrial applications to monitor the health and/or safety of personnel. In such examples, suitable sensors and interrogator devices maybe employed to detect bleeding and/or other trauma to personnel, detect the presence of harmful substances in proximity to personnel or equipment, and/or the like. For example, one or more sensors could be integrated into uniforms or other equipment at any suitable position(s) and be configured to communicate, or cease communications, with an interrogator device upon occurrence of a predetermined environmental condition or change. In these and other examples, one or more interrogator devices could be attached to or carried by vehicles, support equipment, designated team members, site structures, and/or the like.

In other nonexclusive illustrative examples, the technology may be employed for long term monitoring of predetermined environmental conditions or for predetermined environmental changes, in applications where long durations of time may pass before or between occurrences of predetermined environmental conditions or predetermined environmental changes, where long service life, long term, or long shelf life detection of/monitoring for predetermined environmental conditions or predetermined environmental changes may be useful, and/or the like. In these and other applications, the technology may be employed to provide low power monitoring/detection either with no storage of power onboard the sensor or with limited onboard power storage. As one nonexclusive illustrative example, sensors described herein may be configured to be powered from and communicate with an interrogator device if a shield is disrupted/a soluble link is intact.

For example, use of sensors with no onboard power storage may useful in applications in which relatively large sensors have been traditionally employed. For example, such sensors are generally larger than sensors described herein and have limited monitoring times, e.g., before recharging and/or other servicing is needed. In contrast to these other sensors, sensors with no onboard power storage may avoid the disadvantages of sensors with onboard power storage. For example, sensors without onboard power storage may be relatively small, relatively low cost, and/or may be employed for detection of incontinence events over a relatively long or even indefinite time period while also alleviating the disadvantages associated with sensors having onboard power storage. Thus, sensors with no onboard power storage may be useful in a wide variety of applications such as those in which low cost sensors, disposable sensors, light weight sensors, physically small sensors, sensors capable of long term monitoring, and/or the like, may be useful. For example, a small sensor with no onboard power storage may be useful in logistics applications (e.g., monitoring cargo condition during shipping); long term building monitoring (e.g., detecting water or gas line bursts within a wall or other inaccessible area); in vivo monitoring (e.g., monitoring for bodily fluid chemistry change and/or temperature change); and/or the like.

Specific nonlimiting examples of health care applications for the described technology are now discussed below with respect to FIGS. 20 and 21. A nonexclusive illustrative example of a system for detecting the occurrence of an incontinence event is shown generally at 130 in FIG. 20. Unless otherwise specified, system 130 and its various components may, but are not required to, contain at least one of the structure, components, functionality, and/or variations described and/or illustrated herein. As discussed above, system 130 is based on at least one sensor 22/222 that is paired with at least one corresponding interrogator device 24, which is configured to read information that is stored in or on, represented by, or provided by sensor 22/222 if its shield 40/soluble link 242 is in an appropriate condition. System 130 may include a diaper 132 and an interrogator device 24.

Figure 20:
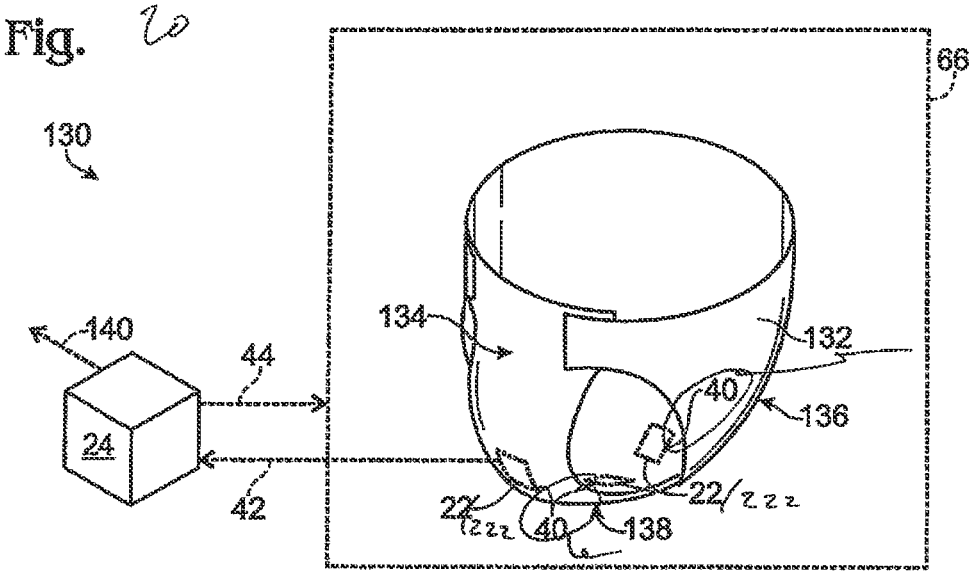
FIG. 20 is a schematic view of an illustrative example of the components of a system for detecting the occurrence of an incontinence event.

As shown in the nonexclusive illustrative example presented in FIG. 20, diaper 132 may include at least one sensor 22/222. The sensors 22/222 may be disposed within diaper 132 such that the sensors are suitably located to detect a fluid, such as urine or fecal matter, discharged by a patient during an incontinence event. For example, at least one sensor 22/222 may be located proximate a frontal region 134 of diaper 132, at least one sensor 22/222 may be located proximate a posterior region 136 of diaper 132, and/or at least one sensor 22/222 may be located proximate a lower region 138 of diaper 132. In some nonexclusive examples, diaper 132 may be configured such that, if diaper 132 is worn by a patient, at least one sensor 22/222, and/or its corresponding shield 40/soluble link 242, is located proximate a urine discharge orifice and/or proximate a fecal discharge orifice of the patient.

During operation of system 130, a patient may be fitted with a diaper 132 that includes at least one suitably located sensor 22/222. The patient may be located such that the patient, or at least diaper 132, is positioned within the interrogation zone 66 of interrogator device 24. In some nonexclusive illustrative examples, the interrogator device 24 may continuously transmit an interrogation signal 44 into the interrogation zone 66. For example, if system 130 is RFID-based, interrogator device 24 may continuously generate an electromagnetic field within interrogation zone 66. When the patient experiences an incontinence event, the discharged fluids may be collected in diaper 132 proximate at least one of the sensors 22/222 and/or its corresponding shield 40/soluble link 242. In one example, the presence of the discharged fluid proximate a sensor 22 and/or its shield 40, may disrupt the shield 40 such that, responsive to the interrogation signal 44, the sensor 22 may transmit an information signal 42 to the interrogator device 24, which may provide an indication 140 of the occurrence of the incontinence event. In another example, the presence of the discharged fluid proximate a sensor 222 and/or its soluble link 242, may disrupt the soluble link 242 such that sensor 222 becomes unresponsive to the interrogation signal 44 from interrogator device 24, which may provide an indication 140 of the occurrence of the incontinence event. In some nonexclusive illustrative examples, information signal 42 may provide an indication of the type of incontinence event or it may provide identification and location information.

A nonexclusive illustrative example of an installed system for detecting the occurrence of an incontinence event is shown generally at 150 in FIG. 20. Unless otherwise specified, system 150 and its various components may, but are not required to, contain at least one of the structure, components, functionality, and/or variations as the other systems for detecting the occurrence of an incontinence event described and/or illustrated herein. System 150 may be installed in a fixed location such as a hospital or nursing home room 152.

System 150 may include at least one interrogator device 24 mounted or otherwise disposed within the room 152. In some nonexclusive illustrative examples of system 150, at least one interrogator device 24 may be configured to continuously transmit an interrogation signal 44 into a fixed interrogation zone 66, such as a zone generally surrounding the bed 154 in which the individual receiving care or patient 156 is located. For example, at least one interrogator device 24 may be fixedly mounted within the room 152 or the bed 154. In some nonexclusive illustrative examples, system 150 may be RFID-based, in which case interrogator device 24 may continuously generate an electromagnetic field within interrogation zone 66.

In some nonexclusive illustrative examples of system 150, at least one interrogator device 24 may be portable, such as to permit usage outside a fixed interrogation zone, e.g., to provide mobile monitoring of sensors 22/222. In some nonexclusive illustrative examples, a portable interrogator device 24 may be a hand-held device, be mounted to a vehicle, or the like. In some nonexclusive illustrative examples, at least one interrogator device 24 may be fixedly mounted to bed 154.

In some nonexclusive illustrative examples of system 150, at least one sensor 22/222 may be mounted within the room 152, such as in a piece of furniture or other location in which the patient 156 may experience an incontinence event. For example, as shown in the nonexclusive illustrative example presented in FIG. 21, at least one sensor 22/222 may be mounted in bed 154, such as within the mattress or sheets.

Figure 21:
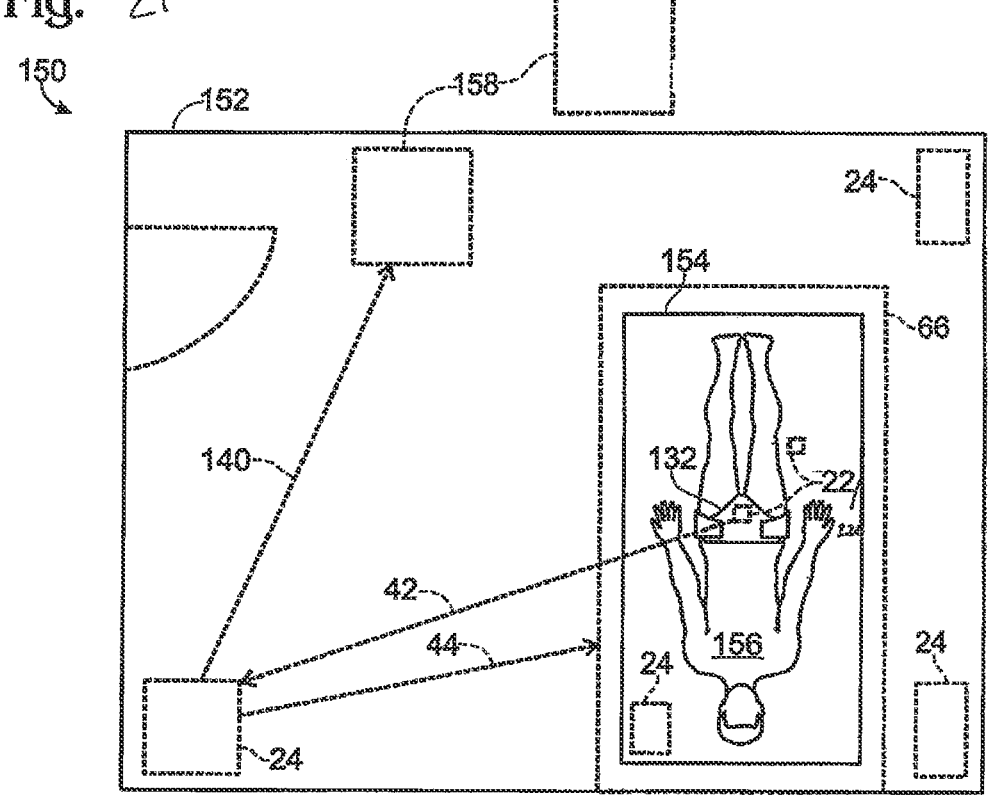
FIG. 21 is a schematic view of an illustrative example of the components of an installed system for detecting the occurrence of an incontinence event.

As shown in the nonexclusive illustrative example presented in FIG. 21, system 150 may include at least one monitoring station 158. Monitoring station 158 may be located at any suitable location where it can receive an indication 140 from at least one of the interrogators 24 that the patient 156 has experienced an incontinence event. Monitoring station 158 may be configured to notify an appropriate party, such as an attendant or nurse, that the patient 156 has experienced an incontinence event. The use of system 150 to provide notification that a patient 156 has experienced an incontinence event may permit an attendant or nurse to become aware of the occurrence of an incontinence event without having to manually examine the patient, which may permit enhanced patient privacy or dignity.

Conclusion

As a nonexclusive illustrative example of operation of a system for detecting environmental conditions or changes, a sensor such as one including a circuit capable of storing, representing, or providing information may be provided. In some nonexclusive illustrative examples, the sensor may be provided with predetermined information stored thereon. The predetermined information may include any suitable combination of information such as location, object or personal identification, details regarding the particular environmental condition or environmental change that exists or has occurred, timing information regarding the duration of the detected environmental condition, elapsed time since the occurrence of the environmental change, or the like.

A non-human interrogator device that is configured to read information stored in or on, represented by or provided by the sensor may be provided. In the case of an RFID-based system for detecting environmental conditions or changes, the interrogator device may continuously generate an electromagnetic field within an interrogation zone.

In certain examples, a shield that has a first condition and a second condition may be provided with the shield provided in the first condition. In some nonexclusive illustrative examples, the shield may be provided proximate the circuit. In the first condition the shield is configured to preclude the interrogator device from reading information stored in or on, represented by or provided by the sensor. In the second condition the shield is configured to enable the interrogator device to read information stored in or on, represented by or provided by the sensor. The shield is configured to transition from the first condition to the second condition if the shield is exposed to a predetermined environmental condition or change, such as the presence of a predetermined fluid.

In other examples, the sensor includes a circuit, an antenna, and a soluble link that has a first condition and a second condition may be provided with the soluble link provided in the first condition. In the first condition the soluble link is configured to enable the interrogator device to read information stored in or on, represented by or provided by the sensor. In the second condition the soluble link is configured to preclude the interrogator device from reading information stored in or on, represented by or provided by the sensor. The soluble link is configured to transition from the first condition to the second condition if exposed to a predetermined environmental condition or change, such as the presence of a predetermined fluid.

During operation of the system, the sensor may be placed into an environment in which there is an interest in detecting environmental conditions or changes, such as a predetermined environmental condition or change, such as the presence of an unexpected and/or undesirable material, such as the presence of an unexpected and/or undesirable fluid. The interrogator device may be positioned such that, if it could read the information stored in or on, represented by or provided by the sensor, it would read the information stored in or on, represented by or provided by the sensor. The interrogator device will attempt to read the information stored in or on, represented by or provided by the sensor. In the case of an RFID-based system for detecting environmental conditions or changes, the interrogator device may continuously attempt to read the information stored in or on, represented by or provided by a sensor located within the interrogation zone. In certain examples, failure of the interrogator device to read the information stored in or on, represented by or provided by the sensor may be used as an indication that a shield is in a first condition because the predetermined environmental condition or change has not occurred and/or is not currently occurring. In other examples, failure of the interrogator device to read the information stored in or on, represented by or provided by the sensor may be used as an indication that a soluble link is in a second condition because the predetermined environmental condition or change has occurred and/or is currently occurring.

In some examples, when the shield and/or the sensor are exposed to the predetermined environmental condition or change, the shield will transition from the first condition to the second condition. Once the shield is in the second condition, the interrogator device will be able to read the information stored in or on, represented by or provided by the sensor, and the interrogator device will read the information that is stored in or on, represented by or provided by the sensor. Based on the information read by the interrogator device from the sensor, the interrogator device may provide an indication that the predetermined environmental condition or change exists and/or has occurred.

In other examples, when the sensor is exposed to the predetermined environmental condition or change, a soluble link will transition from the first condition to the second condition. Once the soluble link is in the second condition, the interrogator device will be unable to communicate with the sensor. Based on an inability of the interrogator device to read from the sensor, the interrogator device may provide an indication that the predetermined environmental condition or change exists and/or has occurred.

In some nonexclusive illustrative examples of using the system for detecting environmental conditions or changes where the system is being used to provide an indication that a person has experienced an incontinence event, the method may include positioning at least one of the sensor and/or the shield proximate at least one of a urine discharge orifice and/or a fecal discharge orifice of a patient. In such an example, the predetermined fluid includes a fluid discharged by the patient during an incontinence event, such as urine or fecal matter.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the disclosure includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A sensor for detecting a predetermined environmental condition, comprising:
   a circuit capable of providing information; and
   a reconfigurable antenna having a radiating element and a soluble link configured to provide a conductive path between the circuit and the antenna, the soluble link having a first condition and a second condition, wherein in the first condition the path is conductive to permit access to information provided by the circuit and, in the second condition the path is non-conductive to prevent access to information provided by the circuit, and wherein the soluble link is configured to transition from the first condition to the second condition if exposed to the predetermined environmental condition.

2. The sensor of claim 1, wherein the soluble link forms at least a portion less than the entirety of the reconfigurable antenna.

3. The sensor of claim 1, wherein in the first condition, the soluble link forms a conductive link between the radiating element and the circuit so that the radiating element is configured to interface the circuit to a radio frequency communication path, and in the second condition the soluble link is non-conductive such that the radiating element is electrically isolated from the circuit.

4. The sensor of claim 1, wherein when the soluble link is in the first condition, the reconfigurable antenna has operational characteristics that are different than operational characteristics of the reconfigurable antenna when the soluble link is in the second condition.

5. The sensor of claim 4, wherein the operational characteristics include a resonant frequency of the reconfigurable antenna.

6. The sensor of claim 1, wherein the reconfigurable antenna is at least one of a stripline antenna or a coil antenna.

7. The sensor of claim 1, wherein the circuit includes an RFID transponder configured to transmit information to an external reader device in response to an interrogation signal from the external reader device, the interrogation signal provides operating power to the RFID transponder, and the soluble link in its second condition is configured to preclude at least one of the provision of operating power from the external reader device to the RFID transponder and the transmission of information from the RFID transponder to the external reader device.

8. The sensor of claim 1, wherein the predetermined environmental condition includes a presence of a predetermined fluid proximate the sensor.

9. The sensor of claim 8, wherein the predetermined fluid includes a fluid discharged by a patient during an incontinence event.

10. The sensor of claim 8, wherein the predetermined fluid includes blood.

11. The sensor of claim 8, wherein at least a portion of the soluble link is at least partially soluble in the predetermined fluid such that the soluble link at least partially transitions from the first condition to the second condition if the at least a portion of the soluble link at least partially dissolves.

12. The sensor of claim 8, wherein the soluble link comprises a conductive layer and an at least partially soluble carrier, the conductive layer is at least partially disposed on the carrier and, in the first condition, is configured to provide an electrical path between the circuit and the radiating element, the at least partially soluble carrier is subject to breakdown when the carrier is exposed to the predetermined fluid, and the breakdown of the carrier at least partially transitions the soluble link from the first condition to the second condition.

13. A sensor for detecting a predetermined environmental condition, comprising:
a circuit capable of providing information; and
a reconfigurable antenna having a radiating element and a soluble link configured to selectively couple the circuit and the antenna, the soluble link having a first condition and a second condition,
wherein in the first condition the soluble link is configured to permit access to information provided by the circuit and, in the second condition the soluble link is configured to prevent access to information provided by the circuit;
wherein the soluble link is configured to transition from the first condition to the second condition if expose to the predetermined environmental condition; and
wherein the predetermined environmental condition includes exposure to a predetermined vapor.

14. A sensor for detecting a predetermined environmental condition, comprising:
a circuit capable of providing information; and
a reconfigurable antenna having a radiating element and a soluble link configured to selectively couple the circuit and the antenna, the soluble link having a first condition and a second condition,
wherein in the first condition the soluble link is configures to permit access to information provided by the circuit and, in the second condition the soluble link is configured to prevent access to information provided by the circuit;
wherein the soluble link is configured to transition from the first condition to the second condition if exposed to the predetermined environmental condition; and
wherein the soluble link comprises a conductive layer, a facilitator, and an at least partially soluble carrier, the conductive layer is at least partially disposed on the carrier and, in the first condition, is configured to provide an electrical path between the circuit and the radiating element, the facilitator is configured to at least partially enable the transition of the soluble link from the first condition to the second condition if the soluble link is exposed to the predetermined environmental condition.

15. The sensor of claim 1, wherein the sensor is configured to communicate with an interrogator device while the soluble link is in the first condition and to cease communications with the interrogator device upon transition of the soluble link to the second condition.

16. The sensor of claim 15, wherein the interrogator device is configured to provide an indication of the condition of the soluble link based upon a loss of communications with the sensor.

17. A sensor for detecting a predetermined environmental condition, comprising:
a circuit configured to wirelessly communicate with an interrogator device via a reconfigurable antenna; and
the reconfigurable antenna, including:
a radiating element configured to interface the circuit to the interrogator device via a radio frequency communication path if there is an electrical connection between the radiating element and the circuit; and
a soluble link which in a first condition electrically connects the circuit to the radiating element and in a second condition electrically disconnects the radiating element from the circuit, and wherein the soluble link is configured to transition from the first condition to the second condition if exposed to the predetermined environmental condition.

18. The sensor of claim 17, wherein in the first condition the soluble link is configured to permit communications between the circuit and the interrogator device and in the second condition the soluble link is configured to prevent communications between the circuit and the interrogator device.

19. The sensor of claim 17, wherein when the soluble link is in the first condition, the reconfigurable antenna has a resonant frequency that is different than another resonant frequency of the reconfigurable antenna when the soluble link is in the second condition.

20. The sensor of claim 17, wherein the radiating element includes at least one of a stripline antenna element or a coil antenna element.

21. The sensor of claim 17, wherein the circuit includes an RFID transponder configured to transmit information to the interrogator device in response to an interrogation signal from the interrogator device, the interrogation signal provides operating power to the RFID transponder, and the soluble link in its second condition is configured to preclude at least one of the provision of operating power from the interrogator device to the RFID transponder and the transmission of information from the RFID transponder to the interrogator device.

22. The sensor of claim 17, wherein the predetermined environmental condition includes a presence of a predetermined fluid or predetermined vapor proximate the sensor.

23. The sensor of claim 17, wherein the sensor is configured to communicate with the interrogator device while the soluble link is in the first condition and to cease communications with the interrogator device upon transition of the soluble link to the second condition, and wherein the interrogator device is configured to provide an indication of the condition of the soluble link based upon a loss of communications with the sensor.

24. A method of detecting a predetermined environmental condition, wherein the method comprises:
transmitting, by an interrogator device, an interrogation signal to a sensor having a reconfigurable antenna including a radiating element and a soluble link, wherein the soluble link in a first condition electrically connects an information-providing circuit to the radiating element and in a second condition electrically disconnects the radiating element from the information-providing circuit, wherein the soluble link is in the first condition prior to exposure to the predetermined environmental condition, and is in the second condition after exposure to the predetermined environmental condition;
receiving, by the interrogator device, in response to transmission of the interrogation signal, an information signal transmitted from the sensor while the soluble link is in the first condition;
transmitting, by the interrogator device, another interrogation signal to the sensor;
detecting, by the interrogator device, a nonresponsiveness of the sensor to the other interrogation signal; and
providing, by the interrogator device, an indication of an occurrence of the predetermined environmental condition based on the detected nonresponsiveness.

25. The method of claim 24, wherein the predetermined environmental condition includes a presence of a predetermined fluid or predetermined vapor proximate the sensor.

26. The method of claim 25, further comprising positioning the sensor proximate at least one of a urine discharge orifice and a fecal discharge orifice of a patient, wherein the predetermined fluid is urine.

27. The method of claim 24, wherein the information-providing circuit includes a passive RFID transponder which transmits the information signal to the interrogator device in response to the interrogation signal, the interrogation signal providing operating power to the RFID transponder, and the soluble link in its second condition precludes at least one of the provisioning of operating power from the interrogator device to the RFID transponder and the transmission of information from the RFID transponder to the interrogator device.

28. The method of claim 24, wherein at least a portion of the soluble link is at least partially soluble in fluid such that the soluble link at least partially transitions from the first condition to the second condition if the at least a portion of the soluble link is at least partially disrupted.

* * * * *

UNITED STATES PATENT AND TRADEMARK OFFICE
CERTIFICATE OF CORRECTION

PATENT NO. : 8,502,684 B2
APPLICATION NO. : 13/011781
DATED : August 6, 2013
INVENTOR(S) : Geoffrey J. Bunza et al.

It is certified that error appears in the above-identified patent and that said Letters Patent is hereby corrected as shown below:

In the Claims

Column 26
Line 66, "...circuit and, ..." should read --... circuit, and....--.

Column 27-28
Line 67-1, "...circuit and, ..." should read --... circuit, and....--.

Column 28
Line 5, "...expose ..." should read --... exposed....--.
Line 17, "...configures ..." should read --... configured....--.
Line 17-18, "...circuit and, ..." should read --... circuit, and....--.

Signed and Sealed this
Fourteenth Day of July, 2015

Michelle K. Lee
*Director of the United States Patent and Trademark Office*